United States Patent [19]

Baker et al.

[11] Patent Number: 5,472,978

[45] Date of Patent: Dec. 5, 1995

[54] AROMATIC COMPOUNDS, PHARMACEUTICAL COMPOSITIONS CONTAINING THEM AND THEIR USE IN THERAPY

[75] Inventors: Raymond Baker, Much Hadham; Angus M. MacLeod; Kevin J. Merchant, both of Bishops Stortford; Christopher J. Swain, Duxford, all of United Kingdom

[73] Assignee: Merck Sharp & Dohme Ltd., Hoddesdon Herts, England

[21] Appl. No.: 162,096

[22] PCT Filed: Jul. 3, 1992

[86] PCT No.: PCTG892/01214

§ 371 Date: Dec. 10, 1993

§ 102(e) Date: Dec. 10, 1993

[87] PCT Pub. No.: WO93/01169

PCT Pub. Date: Jan. 21, 1993

[30] Foreign Application Priority Data

| Jul. 5, 1991 | [GB] | United Kingdom | 9114550 |
| Jul. 10, 1991 | [GB] | United Kingdom | 9114886 |
| Jul. 10, 1991 | [GB] | United Kingdom | 9114888 |
| Jan. 29, 1992 | [GB] | United Kingdom | 9201881 |

[51] Int. Cl.$^6$ .................................................. A61K 31/40
[52] U.S. Cl. .......................... 514/443; 514/469; 514/470; 514/534; 514/539; 514/542; 548/483; 548/484; 548/491; 549/51; 549/57; 549/58; 560/9; 560/11; 560/12; 560/38; 560/39; 560/20; 560/21; 560/22
[58] Field of Search .................................. 514/443, 469, 514/470, 534, 539, 542; 548/483, 484, 491; 560/9, 11, 12, 38, 39, 20, 21, 22; 549/51, 57, 58

[56] References Cited

U.S. PATENT DOCUMENTS

| 2,517,826 | 8/1950 | Avakian et al. | 260/329 |
| 4,390,526 | 6/1983 | Gorecki et al. | 514/535 |
| 4,663,349 | 5/1987 | Repta | 250/329 |

FOREIGN PATENT DOCUMENTS

| 0333174A3 | 9/1989 | European Pat. Off. | 514/443 |
| 0394989A3 | 4/1990 | European Pat. Off. | 514/320 |
| 0443132A1 | 8/1991 | European Pat. Off. | 514/443 |
| 0230151A3 | 7/1992 | European Pat. Off. | 514/443 |
| 1906322 | 2/1969 | Germany | 560/39 |
| 2528069 | 1/1976 | Germany | 514/443 |
| 2054588 | 2/1981 | United Kingdom | 514/443 |

OTHER PUBLICATIONS

Biol. Chem. Hoppe–Seyler, vol. 369, pp. 1307–1315, Dec. 1988, by S. Stoev, et al.
Tetrahedron Letters, vol. 30, No. 43, pp. 5941–5944, 1989, by R. Jackson, et al.
J. Org. Chem., 1990, vol. 55. pp. 6000–6017, by D. Boger, et al.
Bulletin of the Chem. Society of Japan, vol. 40, No. 3, 1967, by S. Sakakibara, et al.
Biochemistry, vol. 24(8) pp. 2040–2047 1985, by T. Tanaka, et al.
J. of Natural Sciences & Math., vol. 24, No. 1, pp. 69–74, Apr. 1984, by Z Malik, et al.
Chem. Abstracts, vol. 83, No. 3, Jul. 21, 1975.
Chem. Abstracts, vol. 60, No. 9, Apr. 27, 1964.
Tetrahedron, vol. 47, No. 26, pp. 4763–4774, 1991, by G. Bourne, et al.
Chem. Abstracts, vol. 94, No. 17, Apr. 27, 1981.
Biochem. Pharmacology, vol. 30, No. 21, pp. 3016–3019 Nov. 1, 1981, by K. Fehske, et al.
Chem. Abstracts, vol. 56, No. 8, Apr. 16, 1962.
J. of Pharmacy & Pharmacology, vol. 39, No. 10, Oct. 1987, pp. 809–818, by D. Cooper, et al.
J. of Steroid Biochemistry, vol. 16, pp. 503–507, 1982, by M. Baker, et al.
Cancer Research, vol. 42, No. 6, pp. 2115–2120, Jun. 1982, by C. Kwong, et al.

*Primary Examiner*—James H. Reamer
*Attorney, Agent, or Firm*—Robert J. North; Melvin Winokur

[57] ABSTRACT

Compounds of formula (I), and salts and prodrugs thereof, wherein Q represents optionally substituted phenyl, naphthyl, indolyl, benzothiophenyl, benzofuranyl, benzyl or indazolyl; Z represents O, S or $NR^8$; X and Y are H or are together =O; $R^1$ and $R^2$ are H; optionally substituted $C_{1-6}$alkyl; optionally substituted phenyl($C_{1-4}$alkyl); $COR^c$; $CO_2R^c$; $CONR^cR^d$; $CONR^cCOOR^d$; or $SO_2R^c$; $R^3$ is H or $C_{1-6}$alkyl, $R^4$ is H, $C_{1-6}$alkyl or optionally substituted phenyl; and $R^5$ represents optionally substituted phenyl; are tachykinin antagonists. They and compositions thereof are useful in therapy.

9 Claims, No Drawings

AROMATIC COMPOUNDS, PHARMACEUTICAL COMPOSITIONS CONTAINING THEM AND THEIR USE IN THERAPY

This application is a 371 of PCT GP92/01214, Jul. 3, 1992.

This invention relates to a class of aromatic compounds which are useful as tachykinin receptor antagonists.

The tachykinins are a group of naturally-occurring peptides found widely distributed throughout mammalian tissues, both within the central nervous system and in the peripheral nervous and circulatory systems. The structures of three known mammalian tachykinins are as follows:

Substance P:

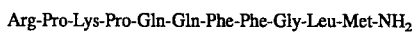

Arg-Pro-Lys-Pro-Gln-Gln-Phe-Phe-Gly-Leu-Met-NH$_2$

Neurokinin. A:

His-Lys-Thr-Asp-Ser-Phe-Val-Gly-Leu-Met-NH$_2$

Neurokinin B:

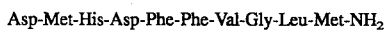

Asp-Met-His-Asp-Phe-Phe-Val-Gly-Leu-Met-NH$_2$

Substance P is believed inter alia to be involved in the neurotransmission of pain sensations [Otsuka et al, "Role of Substance P as a Sensory Transmitter in Spinal Cord and Sympathetic Ganglia" in 1982 Substance P in the Nervous System, Ciba Foundation Symposium 91, 13–34 (published by Pitman) and Otsuka and Yanagisawa, "Does Substance P Act as a Pain Transmitter?" TIPS (Dec. 1987) 8 506–510], specifically in the transmission of pain in migraine (B. E. B. Sandberg et al, J. Med Chem, (1982) 25 1009) and in arthritis [Levine et al in Science (1984) 226 547–549]. These peptides have also been implicated in gastrointestinal (GI) disorders and diseases of the GI tract such as inflammatory bowel disease [Mantyh et al in Neuroscience (1988) 25 (3) 817–37 and D. Regoli in "Trends in Cluster Headache" Ed. Sicuteri et al Elsevier Scientific Publishers, Amsterdam (1987) page 85)]. It is also hypothesised that there is a neurogenic mechanism for arthritis in which substance P may play a role [Kidd et al "A Neurogenic Mechanism for Symmetrical Arthritis" in The Lancet, 11 Nov. 1989 and Grönblad et al "Neuropeptides in Synovium of Patients with Rheumatoid Arthritis and Osteoarthritis" in J. Rheumatol. (1988) 15(12) 1807–10]. Therefore, substance P is believed to be involved in the inflammatory response in diseases such as rheumatoid arthritis and osteoarthritis [O'Byrne et al in Arthritis and Rheumatism (1990) 33 1023–8]. Other disease areas where tachykinin antagonists are believed to be useful are allergic conditions [Hamelet et al Can. J. Pharmacol. Physiol. (1988) 66 1361-7], immunoregulation [Lotz et al Science (1988) 241 1218–21 and Kimball et al, J. Immunol. (1988) 141 (10) 3564–9], vasodilation, Bronchospasm, reflex or neuronal control of the viscera [Mantyh et al, PNAS (1988) 85 3235–9] and, possibly by arresting or slowing β-amyloid-mediated neurodegenerative changes [Yankner et al, Science (1990) 250, 279–82], in senile dementia of the Alzheimer type, Alzheimer's disease and Down's Syndrome. Substance P may also play a role in demyelinating diseases such as multiple sclerosis and amyotrophic lateral sclerosis [J. Luber-Narod et. al., poster to be presented at C.I.N.P. XVIIIth Congress, 28th Jun–2nd Jul., 1992, in press], and in disorders of bladder function such as bladder detrusor hyper-reflexia (Lancet, 16th May, 1992, 1239).

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosis (European patent application no. 0 436 334), ophthalmic diseases such as conjuctivitis, vernal conjunctivitis, and the like, and cutaneous diseases such as contact dermatitis, atropic dermatitis, urticaria, and other eczematoid dermatitis (European patent application no. 0 394 989).

In view of their metabolic instability, peptide derivatives are likely to be of limited utility as therapeutic agents. It is for this reason that non-peptide tachykinin receptor antagonists are sought.

In essence, this invention provides a class of potent non-peptide tachykinin receptor antagonists. By virtue of their non-peptide nature, the compounds of the present invention do not suffer from the shortcomings, in terms of metabolic instability, of known peptide-based tachykinin receptor antagonists.

The following compounds are known:

Inhibition of benzodiazepine receptor binding in vitro by benzyl 3-(3-indolyl)-2-aminopropionate is disclosed in *Biochemical Pharmacology*, 30 (21), 3016–3019 (1981). *Arzneim-Forsch*, 32(I), 684–685 (1982) reports that benzyl 3-(3-indolyl)-2-aminopropionate is an antisickling agent and an inhibitor of glucose transport in human erythrocytes in vitro. A weak inhibition of oestrogen binding to rat alpha-fetoprotein by benzyl 3-(3-indolyl)-2-aminopropionate in vitro is disclosed in *J. Steroid Biochem.*, 16, 503–507 (1982). There is no suggestion in the prior art that benzyl 3-(3-indolyl)-2-aminopropionate is a tachykinin receptor antagonist.

*Australian J. Chem.*, 28(9), 2065–2068 discloses 4-nitrobenzyl 3-(3-indolyl)-2-aminopropionate, 4-nitrobenzyl 2-(1,1-dimethylethoxycarbonylamino)-3-(3-indolylpropionate and benzyl 2-(1,1-dimethylethoxy carbonylamino)-3-(3-indolyl)propionate. There is no suggestion that the disclosed compounds are useful in medicine.

*J. Org. chem.*, 42(8), 1286–1290 (1977) discloses 4-methoxybenzyl 2-(1,1-dimethylethoxycarbonylamino)-3-(3-indolyl)propionate. No medical use is suggested.

Benzyl 3-(3-indolyl)-2-aminopropionate, 2,4,6-trimethylbenzyl 3-(3-indolyl)-2-aminopropionate and 4-nitrobenzyl 3-phenyl-2-aminopropionate are disclosed in *Australia J. Chem.*, 31(8), 1865–1868 (1978). There is no disclosure of a use in medicine.

*Cancer Research*, 42, 2115–2120 (1982) discloses benzyl 3-(3-indolyl)-2-((4-methylphenyl)sulphonylamido) propionate and benzyl 3-phenyl-2-aminopropionate. The compounds were found to inhibit 12-O-tetradecanoylphorbol-13-acetate (TPA) stimulated concanavalin A-mediated cap formation in bovine lymphocytes in vitro. Benzyl 3-phenyl-2-aminopropionate is also disclosed as an antisickling agent and an inhibitor of glucose transport in human erythrocytes in vitro in *Arzneim-Forsch*, 32(I), 684–685 (1982).

Bull.Chem. Soc. Jpn., 40, 646–649 (1967) discloses benzyl 2-(1,1-dimethylpropyloxycarbonylamino)-3-(3-indolyl)propionate. There is no suggestion that the compound is useful in medicine.

4-Nitrobenzyl 2-(1,1-dimethylethoxycarbonylamino)-3-(3-indolyl)propionate and 4-nitrobenzyl-2-acetamido-3-(3-indolyl)propionate are disclosed in *J. Steroid Biochem.*, 16, 503–507 (1982) as inhibitors of oestrogen binding to rat alpha-fetoprotein in vitro.

Benzyl 3-(2-naphthyl)-2-aminopropionate is disclosed in *Bull. Chem. Soc. Jpn*, 63(2), 489–496 (1990). No biological activity is attributed to the compound.

Benzyl 3-(1-naphthyl)-2-aminopropionate is disclosed in *J. phys. Chem*, 94(16), 6237–43 (1990). No biological activity is attributed to the compound.

Benzyl 3-(1-naphthyl)-2-(1,1-dimethylethoxycarbonyl amino)propionate is disclosed in *Tetrahedron Lett.*, 30 (43), 5941–5944 (1989). No biological activity is attributed to the compound.

European Patent application no. 0 443 132 discloses
N-methyl-N-benzyl 3-(2-naphthyl)-2-(1,1-dimethylethoxycarbonylamino)propionamide;
N-methyl-N-(4-fluorobenzyl)-3-(2-naphthyl)-2-(1,1-dimethylethoxycarbonylamino)propionamide;
N-methyl-N-(2-fluorobenzyl)-3-(2-naphthyl)-2-(1,1-dimethylethoxycarbonylamino)propionamide;
N-methyl-N-benzyl-3-(1-naphthyl)-2-(1,1-dimethylethoxycarbonylamino)propionamide;
N-methyl-N-(4-fluorobenzyl)-3-(2-naphthyl)-2-aminopropionamide;
N-methyl-N-(2-fluorobenzyl)-3-(2-naphthyl)-2-aminopropionamide;
N-methyl-N-(3-fluorobenzyl)-3-(2-naphthyl)-2-aminopropionamide;
N-methyl-N-benzyl-3-(2-naphthyl)-2-aminopropionamide;
N-methyl-N-(3-fluorobenzyl)-3-(2-naphthyl)-2-(1,1-dimethylethoxycarbonylamino)propionamide;
as intermediates. No biological activity is attributed to the compounds.

The present invention provides a compound of formula (I), or a salt or prodrug thereof:

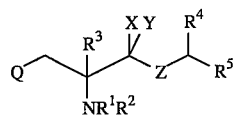

wherein

Q represents optionally substituted phenyl, optionally substituted naphthyl, optionally substituted indolyl, optionally substituted benzthiophenyl, optionally substituted benzofuranyl, optionally substituted benzyl or optionally substituted indazolyl;

Z represents O, S or $NR^8$, where $R^8$ is H or $C_{1-6}$alkyl;

X and Y each represent H or X and Y together form a group =O;

$R^1$ and $R^2$ each independently represent H; $C_{1-6}$alkyl, optionally substituted by hydroxy, cyano, $COR^c$, $CO_2R^c$, $CONR^cR^d$, or $NR^cR^d$ (where $R^c$ and $R^d$ each independently represent H, $C_{1-12}$alkyl or phenyl optionally substituted by one or more of $C_{1-6}$alkyl, $C_{1-6}$alkoxy, halo or trifluoromethyl); phenyl($C_{1-4}$alkyl) (optionally substituted in the phenyl ring by one or more of $C_{1-6}$alkyl, $C_{1-6}$alkoxy, halo and trifluoromethyl); $COR^c$; $C_2R^c$; $CONR^cR^d$; $CONR^cCOOR^d$; or $SO_2R^c$, where $R^c$ and $R^d$ are as above defined;

$R^3$ represents H or $C_{1-6}$alkyl; and $R^4$ represents H, $C_{1-6}$alkyl or phenyl (optionally substituted by 1, 2, or 3 groups selected from $C_{1-6}$alkyl, $C_{2-6}$alkenyl, $C_{2-6}$alkynyl, halo, cyano, nitro, trifluoromethyl, trimethylsilyl $OR^a$, $SR^a$, $SOR^a$, $NR^aR^b$, $NR^aCOR^b$, $NR^aCO_2R^b$, $CO_2R^a$ or $CONR^aR^b$, where $R^a$ and $R^b$ independently represent H, $C_{1-6}$alkyl, phenyl or trifluoromethyl); and $R^5$ represents phenyl (optionally substituted by 1, 2, or 3 groups selected from $C_{1-6}$alkyl, $C_{2-6}$alkenyl, $C_{2-6}$alkynyl, halo, cyano, nitro, trifluoromethyl, trimethylsilyl $OR^a$, $SR^a$, $SOR^a$, $NR^aR^b$, $NR^aCOR^b$, $NR^aCO_2R^b$, $CO_2R^a$ or $CONR^aR^b$, where $R^a$ and $R^b$ independently represent H, $C_{1-6}$alkyl, phenyl or trifluoromethyl);

with the exception of
benzyl 3-(3-indolyl)-2-aminopropionate;
4-nitrobenzyl 3-(3-indolyl)-2-aminopropionate;
4-nitrobenzyl 2-(1,1-dimethylethoxycarbonylamino)-3-(3-indolyl)propionate;
benzyl 2-(1,1-dimethylethoxycarbonylamino)-3-(3-indolyl)propionate;
4-methoxybenzyl 2-(1,1-dimethylethoxycarbonylamino)-3-(3-indolyl)propionate;
2,4,6-trimethylbenzyl 3-(3-indolyl)-2-aminopropionate;
benzyl 3-(3-indolyl)-2-((4-methylphenyl)sulphonamido)propionate;
benzyl 2-(1,1-dimethylpropyloxycarbonylamino)-3-(3-indolyl)propionate;
4-nitrobenzyl 2-acetamido-3-(3-indolyl)propionate; benzyl 3-(1-naphthyl)-2-aminopropionate;
benzyl 3-(1-naphthyl)-2-(1,1-dimethylethoxycarbonylamino)propionate;
benzyl 3-(2-naphthyl)-2-aminopropionate;
N-methyl-N-benzyl 3-(2-naphthyl)-2-(1,1-dimethylethoxycarbonylamino)propionamide;
N-methyl-N-(4-fluorobenzyl)-3-(2-naphthyl)-2-(1,1-dimethylethoxycarbonylamino)propionamide;
N-methyl-N-(2-fluorobenzyl)-3-(2-naphthyl)-2-(1,1-dimethylethoxycarbonylamino)propionamide;
N-methyl-N-benzyl-3-(1-naphthyl)-2-(1,1-dimethylethoxycarbonylamino)propionamide;
N-methyl-N-(4-fluorobenzyl)-3-(2-naphthyl)-2-aminopropionamide;
N-methyl-N-(2-fluorobenzyl)-3-(2-naphthyl)-2-aminopropionamide;
N-methyl-N-(3-fluorobenzyl)-3-(2-naphthyl)-2-aminopropionamide;
N-methyl-N-benzyl-3-(2-naphthyl)-2-aminopropionamide;
N-methyl-N-(3-fluorobenzyl)-3-(2-naphthyl)-2-(1,1-dimethylethoxycarbonylamino)propionamide;
benzyl 3-phenyl-2-aminopropionate; and 4-nitrobenzyl 3-phenyl-2-aminopropionate.

The alkyl, alkenyl and alkynyl groups referred to with respect to any of the above formulae may represent straight, branched or cyclic groups. Thus, for example, suitable alkyl groups include methyl, ethyl, n- or isopropyl, n-, sec-, iso- or tert-butyl, cyclopropyl, cyclobutyl, cyclopentyl or cyclohexyl, and cycloalkyl-alkyl groups such as cyclopropylmethyl; suitable alkenyl groups include vinyl and allyl; and suitable alkynyl groups include propargyl.

The term "halo" as used herein includes fluoro, chloro, bromo and iodo, especially chloro and fluoro.

Where Q represents substituted phenyl, naphthyl, indolyl, benzothiophenyl, benzofuranyl, indazolyl or benzyl, suitable substituents include $C_{1-6}$ alkyl, $C_{2-6}$ alkenyl, $C_{2-6}$ alkynyl, halo, cyano, nitro, trifluoromethyl, trimethylsilyl, , $SR^a$, $SOR^a$, $SO_2R^a$, $OR^a$, $NR^aR^b$, $NR^aCOR^b$, $NR^aCOOR^b$, $COOR^a$ or $CONR^aR^b$, where $R^a$ and $R^b$ are as above defined. One or more substituents may be present and each may be located at any available ring position, except, where $Q^1$ is optionally substituted indolyl or indazolyl, the nitrogen atom. Where $Q^1$ is optionally substituted indolyl or indazolyl, suitable nitrogen substituents include $C_{1-6}$alkyl, optionally substituted phenyl(C$_{1-4}$alkyl), COOR$^a$ or CONR$^a$R$^b$, wherein R$^a$ and R$^b$ are as above defined.

In one embodiment, the present invention provides compounds of formula (IA):

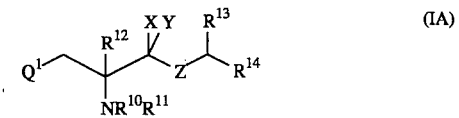

wherein

X, Y and Z are as defined for formula (I);

Q$^1$ represents a phenyl group substituted by one or more halo, or a group Q$^2$ of structure

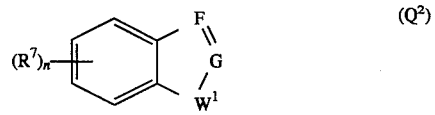

wherein W$^1$ is N—R$^6$, O or S, wherein R$^6$ is H or C$_{1-6}$ alkyl;

F and G either each independently represent N or CH, or both are CH$_2$; and when W$^1$ is N—R$^6$ either F and G are each independently N or CH and the dotted line represents a bond, or F and G are each CH$_2$ and the dotted line is absent, and when W$^1$ is O or S, then F and G are both CH and the dotted line represents a bond;

each R$^7$ may be a substituent on any available position of the ring system of Q$^2$, except on W$^1$, and independently represents C$_{1-6}$ alkoxy, C$_{1-6}$ alkoxy, halo, trifluoromethyl or CONR$^x$R$^y$, wherein R$^x$ and R$^y$ each independently represent H, C$_{1-6}$ alkyl, phenyl or trifluoromethyl;

n is 0, 1, 2 or 3;

R$^{10}$ and R$^{11}$ each independently represent H, C$_{1-6}$ alkyl, phenyl(C$_{1-4}$ alkyl) (optionally substituted in the phenyl ring by one or more of C$_{1-6}$ alkyl, C$_{1-6}$ alkoxy, halo and trifluoromethyl), COR$^z$, COOR$^z$, CONHR$^z$ or SO$_2$R$^z$ where R$^z$ is C$_{1-6}$ alkyl or phenyl (optionally substituted by one or more of C$_{1-6}$ alkoxy, C$_{1-6}$ alkoxy, halo and trifluoromethyl);

R$^{12}$ represents H or C$_{1-6}$ alkyl;

R$^{13}$ represents H, C$_{1-6}$ alkyl or phenyl (optionally substituted by one or more of C$_{1-6}$ alkyl, C$_{2-6}$ alkenyl, C$_{2-6}$ alkynyl, halo, cyano, nitro, trifluoromethyl, SCH$_3$, SOCH$_3$, SO$_2$CH$_3$, OR$^x$, NR$^x$R$^y$, NR$^x$COR$^y$, NR$^x$COOR$^y$, COOR$^x$ or CONR$^x$R$^y$, where R$^x$ and R$^y$ are as above defined);

R$^{14}$ represents a phenyl group which may optionally be substituted by one or more of C$_{1-6}$ alkyl, C$_{2-6}$ alkenyl, C$_{2-6}$ alkynyl, halo, cyano, nitro, trifluoromethyl, SCH$_3$, SOCH$_3$, SO$_2$CH$_3$, OR$^x$, NR$^x$R$^y$, NR$^x$COR$^y$, NR$^x$COOR$^y$, COOR$^x$ or CONR$^x$R$^y$, where R$^x$ and R$^y$ are as above defined;

with the exception of benzyl 3-(3-indolyl)-2-aminopropionate;

4-nitrobenzyl 3-(3-indolyl)-2-aminopropionate;

4-nitrobenzyl 2-(1,1-dimethylethoxycarbonylamino)-3-(3-indolyl)propionate;

benzyl 2-(1,1-dimethylethoxycarbonylamino)-3-(3-indolyl)propionate;

4-methoxybenzyl 2-(1,1-dimethylethoxycarbonylamino)-3-(3-indolyl)propionate;

2,4,6-trimethylbenzyl 3-(3-indolyl)-2-aminopropionate;

benzyl 3-(3-indolyl)-2-((4-methylphenyl)sulphonamido)propionate;

benzyl 2-(1,1-dimethylpropyloxycarbonylamino)-3-(3-indolyl)propionate;

4-nitrobenzyl 2-acetamido-3-(3-indolyl)propionate.

The point of attachment of Q$^2$ may be through any available ring atom, but will preferably be through F or G.

One subgroup of compounds of formula (IA) are compounds wherein R$^{10}$ and R$^{11}$ each independently represent H, C$_{1-6}$ alkyl, phenyl(C$_{1-4}$ alkyl) (optionally substituted in the phenyl ring by one or more of C$_{1-6}$ alkyl, C$_{1-6}$ alkoxy, halo and trifluoromethyl), COR$^z$, COOR$^z$ or CONHR$^z$ where R$^z$ is as previously defined.

Suitable values of the group Q$^1$ include optionally substituted phenyl, 3-indolyl, 1-naphthyl, 2-naphthyl, 3-naphthyl, benzyl, 3-indazolyl, 3-benzothiophenyl and 3-benzofuranyl.

When Q$^1$ is optionally substituted phenyl it preferably represents dichlorophenyl or unsubstituted phenyl, more preferably 3,4-dichlorophenyl.

Preferably Q$^1$ is 3-indolyl or 3-benzothiophenyl.

A preferred subgroup of compounds according to formula (IA) is represented by compounds of formula (IB):

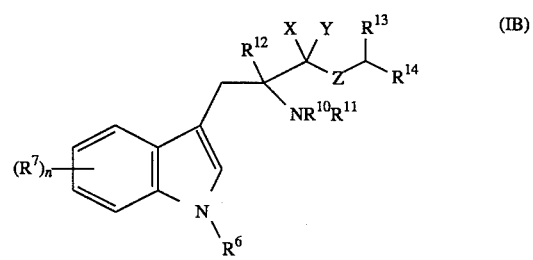

wherein R$^6$, R$^7$, R$^{10}$, R$^{11}$, R$^{12}$, R$^{13}$, R$^{14}$, X, Y, Z and n are each as defined with reference to formula (IA).

A further preferred subgroup of compounds according to formula (IA) is represented by compounds of formula (IC):

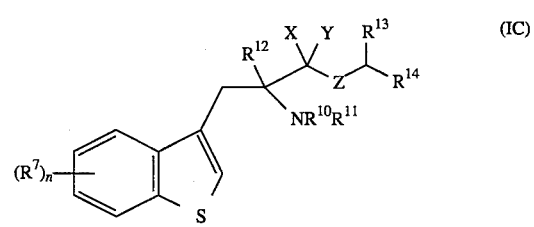

wherein R$^7$, R$^{10}$, R$^{11}$, R$^{12}$, R$^{13}$, R$^{14}$, X, Y, Z and n are each as defined with reference to formula (IA).

In the compounds of the invention it is preferred that X and Y together represent =O.

Preferably Z represents O or NR$^8$, more preferably O.

Preferably at least one of R$^1$ and R$^2$ is other than H. In one preferred group of compounds according to the invention one of R$^1$ and R$^2$ is selected from COR$^c$, CO$_2$R$^c$ and CONR$^c$R$^d$, where R$^c$ and R$^d$ as above defined. Particularly preferred are compounds wherein one of R$^1$ and R$^2$ represents CO(C$_{1-12}$alkyl), or CO(phenyl).

Preferably R$^4$ represents H.

Preferably R$^5$ represents substituted phenyl, especially disubstituted phenyl. More preferably the phenyl substituents will be located in the 3- and 5-positions of the phenyl ring. Suitable phenyl substituents include nitro, trifluoromethyl, trimethylsilyl, bromo, chloro, fluoro, iodo, cyano, methyl, ethyl, cyclopropyl, vinyl, methoxy, phenoxy and amino, preferably trifluoromethyl.

Particularly preferred are compounds wherein $R^5$ represents 3,5-bis(trifluoromethyl)phenyl.

A preferred subgroup of compounds according to the invention is represented by compounds of formula (ID), and salts and prodrugs thereof:

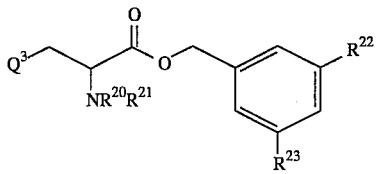

wherein
- $Q^3$ represents 3-indolyl, 3-benzothiophenyl, 3-indazolyl, 1-naphthyl, 2-naphthyl or phenyl optionally substituted by one or more substituents selected from $C_{1-6}$alkyl, $C_{2-6}$alkenyl, $C_{2-6}$alkynyl, halo, cyano, nitro, trifluoromethyl, trimethylsilyl, $SR^a$, $SOR^a$, $SO_2R^a$, $OR^a$, $NR^aR^b$, $NR^aCOR^b$, $NR^aCOOR^b$, $COOR^a$ or $CONR^aR^b$ where $R^a$ and $R^b$ are as defined with reference to formula (I) above;
- $R^{20}$ and $R^{21}$ each independently represent H; $C_{1-6}$alkyl, optionally substituted by hydroxy, cyano, $COR^c$, $CO_2R^c$, $CONR^cR^d$, or $NR^cR^d$ (where $R^c$ and $R^d$ each independently represent H, $C_{1-12}$alkyl or phenyl optionally substituted by one or more of $C_{1-6}$alkyl, $C_{1-6}$alkoxy, halo or trifluoromethyl); phenyl($C_{1-4}$alkyl) (optionally substituted in the phenyl ring by one or more of $C_{1-6}$alkyl, $C_{1-6}$alkoxy, halo and trifluoromethyl); $COR^c$; $CO_2R^c$; $CONR^cR^d$; $CONR^cCOOR^d$; or $SO_2R^c$, where $R^c$ and $R^d$ are as above defined; and
- $R^{22}$ and $R^{23}$ each independently represent $C_{1-6}$alkyl, $C_{2-6}$alkenyl, $C_{2-6}$alkynyl, halo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$, or $CONR^aR^b$, where $R^a$ and $R^b$ independently represent H, $C_{1-6}$alkyl, phenyl or trifluoromethyl).

Preferably $Q^3$ represents 3-indolyl, 3-benzothiophenyl, 3-indazolyl, 1-naphthyl, 2-naphthyl, phenyl or 3,4-dihalophenyl, especially 3,4-dichlorophenyl. According to one subgroup of compounds of formula (ID), $Q^3$ represents 3-indolyl, 3-benzothiophenyl, 3-indazolyl or a phenyl group substituted by one or more halo.

Particularly preferred are compounds of formula (ID) wherein $Q^3$ represents 3-indolyl or 3-benzothiophenyl.

Suitable values for the groups $R^{20}$ and $R^{21}$ include H, $C_{1-6}$ alkyl, especially methyl, $COR^c$ (where $R^c$ is $C_{1-12}$ alkyl, especially $C_{1-6}$alkyl such as methyl or cyclohexyl, or phenyl, especially unsubstituted phenyl), $COOR^c$ where $R^c$ is $C_{1-12}$alkyl, especially $C_{1-4}$alkyl such as, butyl, for example t-butyl and $SO_2R^c$, especially $SO_2CH_3$ or $SO_2$ (phenyl).

In one subgroup of compounds of formula (ID), $R^{20}$ and $R^{21}$ each independently represent H, $C_{1-6}$ alkyl, phenyl($C_{1-4}$alkyl) (optionally substituted in the phenyl ring by one or more of $C_{1-6}$alkyl, $C_{1-6}$alkoxy, halo and trifluoromethyl), $COR^z$, $COOR^z$, $CONHR^z$ or $SO_2R^z$, where $R^z$ is $C_{1-6}$alkyl or phenyl (optionally substituted by one or more of $C_{1-6}$alkyl, $C_{1-6}$alkoxy, halo and trifluoromethyl), such as H, $C_{1-6}$alkyl, phenyl ($C_{1-4}$alkyl) (optionally substituted in the phenyl ring by one or more of $C_{1-6}$alkyl, $C_{1-6}$alkoxy, halo and trifluoromethyl), $COR^z$, $COOR^z$ or $CONHR^z$.

Preferably at least one of $R^{20}$ and $R^{21}$ is other than H. More preferably one of $R^{20}$ and $R^{21}$ represents $COR^c$ where $R^c$ is unsubstituted phenyl or methyl.

Particularly preferred are compounds of formula (ID) wherein $R^{22}$ and $R^{23}$ each represent methyl or trifluoromethyl, more preferably trifluoromethyl.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, oxalic acid, fumaric acid, p-toluenesulphonic acid, maleic acid, succinic acid, acetic acid, trifluoroacetic acid, citric acid, tartaric acid, carbonic acid or phosphoric acid. Salts of amine groups may also comprise quaternary ammonium salts in which the amino nitrogen atom carries a suitable organic group such as an alkyl, alkenyl, alkynyl or aralkyl moiety. Thus, for example, when both $R^1$ and $R^2$ are other than hydrogen, the nitrogen atom to which they are attached may be further substituted to give a quaternary ammonium salt. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

Suitable salts of the compounds of the invention include the hydrochloride, iodide, oxalate, hemi-oxalate, p-toluenesulphonate (tosylate) and trifluoroacetate salts.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H Bundgaard, Elsevier, 1985.

The compounds according to the invention may exist both as enantiomers and as diastereomers. It is to be understood that all such isomers and mixtures thereof are encompassed within the scope of the present invention.

The invention also provides pharmaceutical compositions comprising one or more compounds of formula (I) in association with a pharmaceutically acceptable carrier. Preferably these compositions are in unit dosage forms such as tablets, pills, capsules, powders, granules, sterile parenteral solutions or suspensions, or suppositories, for oral, parenteral or rectal administration. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action.

For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

The following group of compounds of formula (I) are hereinafter referred to as Group A:
benzyl 3-(3-indolyl)-2-aminopropionate;
4-nitrobenzyl 3-(3-indolyl)-2-aminopropionate;
4-nitrobenzyl 2-(1,1-dimethylethoxycarbonylamino)-3-(3-indolyl)propionate;
benzyl 2-(1,1-dimethylethoxycarbonylamino)-3-(3-indolyl)propionate;
4-methoxybenzyl 2-(1,1-dimethylethoxycarbonylamino)-3-(3-indolyl)propionate;
2,4,6-trimethylbenzyl 3-(3-indolyl)-2-aminopropionate;
benzyl 3-(3-indolyl)-2-((4-methylphenyl)sulphonamido)propionate;
benzyl 2-(1,1-dimethylpropyloxycarbonylamino)-3-(3-indolyl)propionate;
4-nitrobenzyl 2-acetamido-3-(3-indolyl)propionate; benzyl 3-(1-naphthyl)-2-aminopropionate;
benzyl 3-(1-naphthyl)-2-(1,1-dimethylethoxycarbonylamino)propionate;
benzyl 3-(2-naphthyl)-2-aminopropionate;
N-methyl-N-benzyl 3-(2-naphthyl)-2-(1,1-dimethylethoxycarbonylamino)propionamide;
N-methyl-N-(4-fluorobenzyl)-3-(2-naphthyl)-2-(1,1-dimethylethoxycarbonylamino)propionamide;
N-methyl-N-(2-fluorobenzyl)-3-(2-naphthyl)-2-(1,1-dimethylethoxycarbonylamino)propionamide;
N-methyl-N-benzyl-3-(1-naphthyl)-2-(1,1-dimethylethoxycarbonylamino)propionamide;
N-methyl-N-(4-fluorobenzyl)-3-(2-naphthyl)-2-aminopropionamide,
N-methyl-N-(2-fluorobenzyl)-3-(2-naphthyl)-2-aminopropionamide;
N-methyl-N-(3-fluorobenzyl)-3-(2-naphthyl)-2-aminopropionamide;
N-methyl-N-benzyl-3-(2-naphthyl)-2-aminopropionamide;
N-methyl-N-(3-fluorobenzyl)-3-(2-naphthyl)-2-(1,1-dimethylethoxycarbonylamino)propionamide;
benzyl 3-(3-indolyl)-2-aminopropionate; and
4-nitrobenzyl 3-(3-indolyl)-2-aminopropionate.
Pharmaceutical compositions comprising one or more compounds of Group A in association with a pharmaceutically acceptable carrier are included within the scope of the present invention.

The present invention further provides a process for the preparation of a pharmaceutical composition comprising a compound of formula (I) which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity. These may include disorders of the central nervous system such as anxiety, depression, psychosis and schizophrenia; neurodegenerative disorders such as dementia, including senile dementia of the Alzheimer type, Alzheimer's disease and Down's syndrome; demyelinating diseases such as MS and ALS and other neuropathological disorders such as peripheral neuropathy, such as diabetic and, chemotherapy-induced neuropathy, and postherpetic and other neuralgias; respiratory diseases such as chronic obstrucutive airways disease, bronchopneumonia, bronchospasm and asthma; inflammatory diseases such as inflammatory bowel disease, psoriasis, fibrositis, osteoarthritis and rheumatoid arthritis; allergies such as eczema and rhinitis; hypersensitivity disorders such as poison ivy; ophthalmic diseases such as conjunctivitis, vernal conjunctivitis, and the like; cutaneous diseases such as contact dermatitis, atropic dermatitis, urticaria, and other eczematoid dermatitis; addiction disorders such as alcoholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal (GI) disorders and diseases of the GI tract such as disorders associated with the neuronal control of viscera such as ulcerative colitis, Crohn's disease and incontinence; disorders of bladder function such as bladder detrusor hyper-reflexia; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine. For example, the compounds of formula (I) may suitably be used in the treatment of disorders of the central nervous system such as anxiety, psychosis and schizophrenia; neurodegenerative disorders such as senile dementia of the Alzheimer type, Alzheimer's disease and Down's syndrome; respiratory diseases such as bronchospasm and asthma; inflammatory diseases such as inflammatory bowel disease, osteoarthritis and rheumatoid arthritis; adverse immunological reactions such as rejection of transplanted tissues; gastrointestinal (GI) disorders and diseases of the GI tract such as disorders associated with the neuronal control of viscera such as ulcerative colitis, Crohn's disease and incontinence; disorders of blood flow caused by vasodilation; and pain or nociception, for example, that attributable to or associated with any of the foregoing conditions or the transmission of pain in migraine.

The compounds of formula (I) are particularly useful in the treatment of pain or nociception and/or inflammation and disorders associated therewith such as, for example, neuropathy, such as diabetic and chemotherapy-induced neuropathy, postherpetic and other neuralgias, asthma, osteoarthritis, rheumatoid arthritis and especially migraine.

The present invention further provides a compound of formula (I), for use in therapy. Included in the present invention is the provision of a compound selected from Group A for use in therapy.

Alternatively, the present invention provides a compound selected from:

4-nitrobenzyl-3-(3-indolyl)-2-aminopropionate; benzyl-(1,1-dimethylethoxycarbonylamino)-3-(3-indolyl)propionate;
4-methoxybenzyl 2-(1,1-dimethylethoxycarbonylamino)-3-(3-indolyl)propionate;
2,4,6-trimethylbenzyl 3-(3-indolyl)-2-aminopropionate; benzyl-2-(1,1-dimethylpropyloxycarbonylamino)-3-(3-indolyl)propionate;
benzyl 3-(1-naphthyl)-2-aminopropionate;
benzyl 3-(1-naphthyl)-2-(1,1-dimethylethoxycarbonylamino)propionate;
benzyl 3-(2-naphthyl)-2-aminopropionate;
N-methyl-N-benzyl 3-(2-naphthyl)-2-(1,1-dimethylethoxycarbonylamino)propionamide;
N-methyl-N-(4-fluorobenzyl)-3-(2-naphthyl)-2-(1,1-dimethylethoxycarbonylamino)propionamide;
N-methyl-N-(2-fluorobenzyl)-3-(2-naphthyl)-2-(1,1-dimethylethoxycarbonylamino)propionamide;
N-methyl-N-benzyl-3-(1-naphthyl)-2-(1,1-dimethylethoxycarbonylamino)propionamide;
N-methyl-N-(4-fluorobenzyl)-3-(2-naphthyl)-2-aminopropionamide;
N-methyl-N-(2-fluorobenzyl)-3-(2-naphthyl)-2-aminopropionamide;
N-methyl-N-(3-fluorobenzyl)-3-(2-naphthyl)-2-aminopropionamide;
N-methyl-N-benzyl-3-(2-naphthyl)-2-aminopropionamide;
N-methyl-N-(3-fluorobenzyl)-3-(2-naphthyl)-2-(1,1-dimethylethoxycarbonylamino)propionamide;
L-benzyl 3-phenyl-2-aminopropionate;
L-4-nitrobenzyl 3-phenyl-2-aminopropionate.
4-nitrobenzyl-3-phenyl-2-aminopropionate, for use in therapy.

According to a further or alternative aspect, the present invention provides a compound of formula (I) for use in the manufacture of a medicament for the treatment of physiological disorders associated with an excess of tachykinins, especially substance P. It is to be understood that among the compounds of formula (I) which the present invention provides for use in the manufacture of a medicament for the treatment of disorders associated with an excess of tachykinins are compounds of Group A.

For example, the present invention provides the use of a compound selected from:
benzyl 3-(3-indolyl)-2-aminopropionate;
benzyl-3-(3-indolyl)-2-((4-methylphenyl)sulphonamido)propionate;
4-nitrobenzyl 2-(1,1-dimethylethoxycarbonylamino)-3-(3-indolyl)propionate;
4-nitrobenzyl 2-acetamido-3-(3-indolyl)propionate; benzyl 3-phenyl 2-aminopropionate;
for the manufacture of a medicament for the treatment of disorders associated with an excess of tachykinins.

In particular, the present invention provides a compound of formula (I) for the manufacture of a medicament for the treament of pain or inflammation and disorders associated therewith.

The present invention also provides a method for the the treatment or prevention of physiological disorders associated with an excess of tachykinins, especially substance P, which method comprises administration to a patient in need thereof of a tachykinin reducing amount of a compound of formula (I), or a composition comprising a compound of formula (I). It is to be understood that such method includes a method wherein the compound of formula (I) is selected from compounds of Group A.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day. For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

The compounds according to the invention wherein Z is O or S may be prepared from intermediates of formula (II):

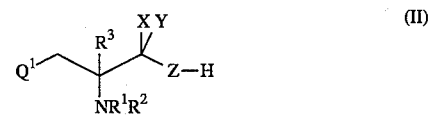

wherein $R^1$, $R^2$, $R^3$, $Q^1$, X and Y are as defined for formula I, and Z is O or S, by reaction with a compound of formula Hal-CHR$^4$R$^5$, where $R^4$ and $R^5$ are as defined for formula (I) and Hal is halo, such as bromo, chloro or iodo, in the presence of a base.

Favoured bases of use in the reaction are caesium carbonate and sodium hydride. Conveniently the reaction is effected in a suitable organic solvent, such as an alcohol, for example, methanol, or an anhydrous solvent, for example, anhydrous dimethylformamide. Compounds of formula (II) wherein both $R^1$ and $R^2$ represent H may require replacement of either $R^1$ or $R^2$ by a protecting group for the duration of the reaction.

The compounds of formula (I) wherein Z is NR$^8$ and X and Y together represent =O may be prepared from intermediates of formula (II) wherein Z is O and X and Y together represent =O (formula (IIA)) by reaction with compounds of formula HNR$^8$—CHR$^4$R$^5$, wherein $R^4$, $R^5$ and $R^8$ are as defined for formula (I). Preferably, the reaction is effected in the presence of a coupling agent, such as dicyclohexylcarbodiimide.

Compounds according to the invention wherein X and Y both represent H and Z represents S may also conveniently be prepared by conversion of the hydroxyl group of compounds of formula (II) wherein X and Y both represent hydrogen and Z is O to a leaving group, for example, by reaction with mesyl chloride or tosyl chloride, followed by reaction with a compound of formula R$^4$R$^5$HCSH, in the presence of a base. Suitable bases include, for example, metal hydrides, such as sodium hydride. The reaction is conveniently effected in an anhydrous organic solvent, such as anhydrous dimethylformamide.

The compounds according to the invention wherein Z is NR$^8$ and X and Y both represent H may be prepared from the corresponding compounds of formula (I) wherein X and Y together represent =O by reduction. Suitable reducing agents include, for example, metal hydrides, such as lithium aluminium hydride, and borane. Conveniently the reaction is effected in a suitable organic solvent, such as an ether, for example, tetrahydrofuran.

Intermediates of formula (IIA) (i.e. wherein Z is O and X and Y together represent =O) are commercially available or may be prepared by standard syntheses of amino acids. Such syntheses are well known to persons skilled in the art and are described, for example, in *Chemistry and Biochemistry of the Amino Acids*, ed. G. C. Barrett, Chapman and Hall, 1985.

Intermediates of formula (II) wherein X and Y are H and Z is S may be prepared from the corresponding intermediates of formula (II) wherein Z is O by treating the latter compound with Lawesson's reagent or phosphorus pentasulphide in a suitable solvent, e.g. pyridine, at ambient or elevated temperature, suitably at the reflux temperature of the chosen solvent.

Intermediates of formula (II) where X and Y are =O and Z is S may be prepared from the corresponding compounds of formula (IIA) by reaction with thionyl chloride, to give an acyl chloride, followed by treatment with hydrogen sulphide.

Intermediates of formula (II) wherein X and Y both represent H may be prepared from intermediates of formula (II) wherein X and Y together represent =O by reduction. Suitable reagents and procedures will be readily apparent to persons skilled in the art.

Compounds of formula (I) may also be prepared from other compounds of formula (I). Thus, for example, compounds of formula (I) wherein one or both of $R^1$ and $R^2$ represent H may be reacted with an optionally substituted alkylating agent or an acylating agent to produce compounds of formula (I) wherein one or both of $R^1$ and $R^2$ represent an optionally substituted alkyl group or an acyl group. Suitable procedures are described in the accompanying examples, or will be readily apparent to one skilled in the art.

Conversely, compounds of formula (I) wherein one or both of $R^1$ and $R^2$ represent, for example, an acyl or a benzyl group, may be converted to compounds of formula (I) wherein one or both of $R^1$ and $R^2$ represent H by, for example, hydrolysis or catalytic hydrogenation. Suitable reagents and conditions are decribed in the accompanying examples, or will be readily apparent to one skilled in the art of organic chemistry.

Where the above-described processes for the preparation of the compounds according to the invention give rise to mixtures of stereoisomers, these isomers may be separated, suitably by conventional techniques such as preparative chromatography.

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wutts, *Protective Groups in Organic Synthesis*, John Wiley & Sons, 1991. The protecting groups may be removed at a convenient subsequent stage using methods known from the art.

The following non-limiting Examples illustrate the preparation of compounds according to the invention.

EXAMPLE 1

3,5-Dimethylbenzyl 2-(1,1-dimethylethoxycarbonylamino)-3-(3-indolyl)propionate

N α BOC-L-Tryptophan (7.6 g) was dissolved in methanol (100 ml) and water (10 ml). Cesium carbonate (4.05 g) in water (50 ml) was added and the solvent was removed in vacuo. The residue was azeotroped with anhydrous dimethylformamide (2×100 ml). 3,5-Dimethylbenzyl bromide (5.0 g) in dimethylformamide (10 ml) was added to a solution of the cesium salt in dimethylformamide (100 ml) and the reaction was stirred for 16 hours. The solvent was removed in vacuo and the residue was partitioned between ethyl acetate and water. The organic phase was dried (MgSO$_4$) and the solvent was removed in vacuo to give a solid which was recrystallised from ethyl acetate/petroleum ether to yield the title compound as a white solid (6.83 g). m.p. 152°–153° C. $^1$H NMR (360 MHz, CDCl$_3$) δ 8.00 (1H, s), 7.54 (1H, d, J=8 Hz), 7.32 (1H, d, J=8 Hz), 7.16 (1H, t, J=7 Hz), 7.09 (1H, t, J=7 Hz), 6.95 (1H, s), 6.64 (3H, s), 5.09–5.07 (1H, m), 5.00 (2H, m), 4.70–4.67 (1H, m), 3.29–3.28 (1H, m), 2.29 (6H, s), 1.42 (9H, s). Found: C, 70.51; H, 7.28; N, 6.53 C$_{25}$H$_{30}$N$_2$O$_4$. 0.25 (H$_2$O) requires C, 70.32; H, 7.20; N, 6.56%.

EXAMPLE 2

2-Methoxybenzyl 2-(1,1-dimethylethoxycarbonylamino)-3-(3-indolyl)propionate

Following the method of Example 1, 2-methoxybenzyl chloride (3.9) and N α BOC-L-tryptophan (7.6 g) gave the title compound which was recrystallised from ethyl acetate/petroleum ether (3.4 g), m.p. 132°–133° C. $^1$H NMR (360 MHz, CDCl$_3$) δ7.99 (1H, s), 7.56 (1H, d, J=Hz), 7.33–7.07 (5H, m), 6.93–6.66 (3H, m), 5.21–5.07 (3H, m), 4.70–4.67 (1H, m), 3.01 (3H, s), 3.30 (1H, m), 1.41 (9H, s). Found: C, 67.91; H, 6.65; N, 6.60; C$_{24}$H$_{28}$N$_2$O$_5$ requires C, 68.00; H, 6.70; N, 6.66%.

EXAMPLE 3

Benzyl 2-(1,1-dimethylethoxycarbonylamino)-3-(3-indolyl))propionate

Following the method of Example 1, benzyl bromide (0.85 g) and N-α-BOC-L-tryptophan (1.52 g) gave the title compound which was recrystallised from ethyl acetate/petroleum ether (1.3 g), m.p. 132°–133° C. $^1$H NMR (360 MHz, CDCl$_3$) 7.99 (1H, s), 7.54 (1H, d, J=7 Hz), 7.33–7.07 (8H, m), 6.60 (1H, s), 5.07 (2H, d, J=7 Hz), 4.68–4.64 (1H, m), 3.29–3.27 (1H, m), 1.42 (9H, s). Found: C, 70.03; H, 6.64; N, 7.10; C$_{23}$H$_{26}$N$_2$O$_4$ requires C, 69.93; H, 6.84; N, 7.12%.

EXAMPLE 4

3,5-Dimethybenzyl 2-acetamido-3-(3-indolyl)propionate a) 3,5-Dimethylbenzyl 2-amino-3-(3-indolyl)propionate Hydrochloride 3,5-Dimethylbenzyl 2-(1,1-dimethylethoxycarbonylamino)-3-(3-indolyl)propionate (1.0 g) was dissolved in dry tetrahydrofuran (20 ml). Saturated methanolic hydrochloric acid (10 ml) was added and the reaction was stirred for 16 hours. The solvent was removed in vacuo and the residue was recrystallised from ethanol/diethyl ether to yield 3,5-dimethylbenzyl 2-amino-3-(3-indolyl)propionate hydrochloride (0.71 g), m.p. 213°–214° C. $^1$H NMR (360 MHz D$_6$ DMSO) δ11.09 (1H, s), 8.64 (1H, s), 7.51 (1H, d, J=7 Hz), 7.38 (1H, d, J=7 Hz), 7.20 (1H, d, J=2 Hz), 7.10 (1H, t, J=7 Hz), 6.98 (1H, t, J=7 Hz), 6.94 (1H, s), 6.76 (2H, s). Found:

C, 66.25; H, 6.67; N, 7.71, $C_{20}H_{22}N_2O_2$. HCl. 0.25($H_2O$) requires C, 66.11; H, 6.52; N, 7.71%.

b) 3,5-Dimethylbenzyl 2-acetamido-3-(3-indolyl)propionate

The product of part (a) (500 mg) was dissolved in dry pyridine (500 μL) and acetic anhydride (500 μL) was added. The reaction was stirred for 16 hours and then ethyl acetate (50 ml) was added. The solution was washed with hydrochloric acid (5N, 50 ml), brine (50 ml) and water (50 ml). The organic phase was dried ($MgSO_4$), filtered and the solvent was removed in vacuo to yield an oil which was purified by chromatography on silica gel using ethyl acetate/petroleum ether (3:2) to yield the title compound as a white solid (0.17 g), m.p. 145°–146° C. $^1$HMR (360 MHz, $CDCl_3$) δ8.19 (1H, s), 7.51 (1H, d, J=7 Hz), 7.33 (1H, d, J=7 Hz), 7.18 (1H, t, J=7 Hz), 7.09 (1H, t, J=7 Hz), 6.97 (1H, s) 6.87 (2H, s), 6.77 (1H, d, J=2 Hz), 6.03 (1H, d, J=8 Hz), 5.06–4.97 (3H, m), 3.37–3.26 (2H, m), 2.30 (6H, s), 1.94 (3H, s). Found: C, 71.62; H, 6.69; N, 7.59, $C_{22}H_{24}N_2O_3$. 0.25($H_2O$) requires C, 71.56; H, 6.88; N, 7.50%.

EXAMPLE 5

3,5-Dimethylbenzyl 2-cyclohexanecarboxamido-3-(3-indolyl)propionate

Following the method of Example 4b) cyclohexyl carbonyl chloride (500 μL) and 3,5-dimethylbenzyl 2-amino-3-(3-indolyl)propionate indolyl)propionate hydrochloride (500 mg) gave the title compound after chromatography on silica using ethyl acetate/petroleum ether (1:4) (0.18 g), m.p. 143°–144° C. $^1$H NMR (360 MHz, $CDCl_3$) δ8.11 (1H, s), 7.52 (1H, d, J=7 Hz), 7.34 (1H, d, J=7 Hz), 7.18 (1H, t, J=7 Hz), 7.09 (1H, t, J=7 Hz), 6.96 (1H, s), 6.86 (2H, s), 6.60 (1H, d, J=2 Hz), 5.97 (1H, d, J=8 Hz), 5.02–4.97 (3H, m), 3.31 (2H, d, J=5 Hz), 2.30 (6H, s), 2.07–1.96 (1H, m), 1.80–1.10 (10H, m). Found: C, 74.35; H, 7.49; N, 6.42; $C_{27}H_{32}N_2O_3$. 0.2 ($H_2O$) requires C, 74.51; H, 7.53; N, 6.47%.

EXAMPLE 6

3,5-Dimethylbenzyl 3-(3-indolyl)-2-benzamidopropionate

Following the method of Example 4b), benzoyl chloride (500 μL) and 3,5-dimethylbenzyl 2-amino-3-(3-indolyl)propionate hydrochloride (500 mg) gave the title compound after chromatography on silica using ethyl acetate/petroleum ether (3:2) (0.21 g), m.p. 133°–134° C. $^1$H NMR (360 MHz, $CDCl_3$) δ8.10 (1H, s), 7.67 (1H, d, J=7 Hz), 7.53 (1H, d, J=7 Hz), 7.49–7.25 (4H, m), 7.17 (1H, t, J=7 Hz), 7.05 (1H, t, J=7 Hz), 6.97 (1H, s), 6.89 (2H, s), 6.82 (1H, d, J=2 Hz), 6.68 (1H, d, J=8 Hz), 5.18 (1H, m), 5.06 (2H, s), 3.45 (2H, m), 2.3 (6H, s). Found: C, 75.24; H, 6.20; N, 6.50; $C_{27}H_{26}N_2O_3$. 0.25($H_2O$) requires C, 74.90; H, 6.22; N, 6.51%.

EXAMPLE 7

3,5-Dimethylbenzyl 2-(N,N-dimethylamino)-3-(3-indolyl)propionate Hydrochloride 3,5-Dimethylbenzyl 2-amino-2-(3-indolyl)propionate hydrochloride salt (500 mg) was dissolved in methanol (30 ml) and sodium cyanoborohydride (220 mg) and acetic acid (1 ml) were added. The reaction was cooled to 0° C. and formaldehyde solution (38% w/v, 300 mg) in methanol (20 ml) was added over 0.25 hours. The reaction was stirred for 2 hours and then the solvents were removed in vacuuo. The residue was partitioned between dichloromethane and saturated sodium bicarbonate solution. The organic extract was dried and evaporated to yield an oil which was purified by column chromatography on silica using ethyl acetate/petroleum ether (4:1). The oil thus obtained was treated with methanolic hydrochloric acid and the solvent was removed to yield the title compound as a white solid (95 mg), m.p. 129°–130° C. $^1$H NMR (360 MHz, $D_6$ DMSO) δ11.11 (1H, s), 7.64 (1H, d, J=7 Hz), 7.39 (1H, d, J=7 Hz), 7.16 (1H, d, J=2 Hz), 7.11 (1H, t, J=7 Hz), 7.01 (1H, t, J=7 Hz), 6.88 (1H, s), 6.55 (2H, s), 4.95 (1H, d, J=12 Hz), 4.81 (1H, d, J=12 Hz), 4.38–3.28 (2H, m), 2.91 (6H, m), 2.17 (6H, s). Found: C, 66.19; H, 6.96; N, 6.98; $C_{22}H_{26}N_2O_2$. HCl.0.6($H_2O$) requires C, 66.43; H, 7.14; N, 7.04%.

EXAMPLE 8

3,5-Dimethylbenzyl 3-(3-indolyl)-2-(N,N,N-trimethylamino)propionate Iodide 3,5-Dimethylbenzyl 2-(N,N-dimethylamino)-3-(3-indolyl)propionate (500 mg) was dissolved in acetone (1 ml) and diethyl ether (2.0 ml). Iodomethane was added and the reaction was stirred for 16 hours. The precipitate which had formed was filtered and dried to yield the title compound (350 mg), m.p. 164°–165° C., $^1$H NMR (360 MHz, $D_6$ DMSO), δ11.07 (1H, s), 7.56 (1H, d, J=7 Hz), 7.41 (1H, d, J=7 Hz), 7.18–7.03 (3H, m), 6.67 (1H, s), 6.42 (2H, s), 4.90 (1H, d, J=12Hz), 4.75 (1H, d, J=12Hz), 4.62–4.58 (1H, m), 3.66–3.61 (1H, m), 3.31 (9H, s), 3.38–3.29 (1H, m), 2.14 (6H, s). Found: C, 55.69; H, 6.12; N, 5.65 $C_{23}H_{30}N_2O_2I$ requires C, 55.99; H, 6.13; N, 5.68%.

EXAMPLE 9

Diphenylmethyl 2-acetamido-3-(3-indolyl)propionate

Following the method of Example 1, bromodiphenyl methane (5.0 g) and N-acetyl-D,L-tryptophan (5.0 g) gave the title compound which was recrystallised from diethyl ether (2.2 g), m.p. 147°–148° C., $^1$H NMR (360 MHz, $CDCl_3$) δ7.88 (1H, s), 7.47 (1H, d, J=7 Hz), 7.34–7.28 (15H, m), 6.67 (1H, s), 6.40 (1H, d, J=2 Hz), 5.95 (1H, d, J=7 Hz), 5.14–5.09 (1H, m), 3.40–5.09 (2H, m), 1.91 (3H, s). Found: C, 75.53; H, 6.04; N, 6.88 $C_{26}H_{24}N_2O_3$ requires C, 75.71; H, 5.86; N, 6.79%.

EXAMPLE 10

3,5-Bistrifluoromethylbenzyl-2-acetamido-3-(3-benzo[b]thienyl)propionate

Anhydrous caesium carbonate was added to a solution of N-acetyl-β-(3-benzo[b]thienyl)-DL-alanine (473 mg) [P. N. Rao et al., Int. J. Peptide Protein Res. 29, 118–125, 1987] in dry methanol (50 ml). The solution was stirred at room temperature for 30 minutes, diluted with toluene (50 ml) and the solvent removed under reduced pressure. The resulting product was re-dissolved in dry DMF (50 ml) and 3,5-bistrifluoromethylbenzyl bromide (0.65 ml) added. The solution was stirred at room temperature for 24 hours, diluted with water (100 ml) and extracted with diethyl ether (2×100 ml). The organic layers were separated, dried over ($MgSO_4$), filtered and the solvent removed under reduced pressure. Recrystallisation from isopropanol afforded the title compound as colourless needles, mp 129°–130° C., $^1$H NMR δ (CDCl$_3$) 1.97 (3H, s, NHCOC$\underline{H}_3$), 3.44 (1H, t, J=6.0 Hz, NHC$\underline{H}$CO$_2$), 5.02 (1H, d, J=8.0 Hz, OC$\underline{H}$H-Ar), 5.04 (1H, d, J=7.0 Hz, C$\underline{H}$HCHCO$_2$), 5.06 (1H, d, J=7.0 Hz, CH$\underline{H}$CHCO$_2$), 5.12 (1H, d, J=8.0 Hz, OCH$\underline{H}$-Ar), 6.00 (1H, s, N$\underline{H}$COCH$_3$), 7.25 (1H, s, SC$\underline{H}$C), 7.36 (2H, m, Ar-H), 7.60 (2H, s, Ar-H), 7.72 (1H, m, Ar-H), 7.75 (1H, m, Ar-H), 7.82 (1H, m, Ar-H). m/z (EI$^+$) 489. Found: C, 53.70; H, 3.50; N, 2.86; C$_{22}$H$_{17}$NO$_3$SF$_6$ requires C, 53.99; H, 3.84; N, 2.86%.

EXAMPLE 11

3,5-Bistrifluoromethylbenzyl-2-acetamido-3-(3-indazolyl)propionate

Caesium carbonate (82 mg) was added to a solution of 2-acetamido-3-(3-indazolyl)propionic acid (200 mg) [H. R. Snyder et al., J. Amer. Chem. Soc. 74, 2009, 1952] in dry methanol (10 ml). The resulting solution was stirred for 30 minutes at room temperature and then reduced to dryness in vacuo. The recovered white solid was redissolved in dry dimethylformamide (5 ml) and treated with 3,5-bistrifluoromethylbenzyl bromide (92 mg). The resulting solution was stirred at room temperature for 18 hours. The reaction mixture was diluted with water (50 ml) and extracted into ethyl acetate (50 ml). The organic layers were separated, dried (MgSO$_4$), filtered and the solvent removed under reduced pressure. Recrystallisation from isopropenol afforded the title compound, mp 120° C. (dec.). (360 MHz, DMSO) $^1$H NMR δ1.99 (3H, s, NCOC$\underline{H}_3$), 3.45 (1H, m, OCHHAr), 3.66 (1H, m, OCHHAr), 5.11 (3H, m, NC$\underline{H}$CO and CHC$\underline{H}_2$), 8.75 (1H, bs, CH$_3$CON$\underline{H}$), 7.14 (1H, m, ArH), 7.25 (3H, m, ArH0, 7.40 (1H, m, ArH), 7.57 (2H, s, CF$_3$CHC$\underline{H}_2$), 7.67 (1H, s, CF$_3$C$\underline{H}$CF$_3$); m/z 473 (M$^+$); Found: C, 53.57; H, 3.57; N, 8.87; C$_{21}$H$_{17}$N$_3$O$_3$F$_6$ requires C, 53.28; H, 3.62; N, 8.63%.

EXAMPLE 12

2-Trifluoromethylbenzyl 3-(3-indolyl)-2-benzamidopropionate

To a suspension of L-Tryptophan (5.1 g) in saturated aqueous sodium carbonate solution (100 ml) was added a solution of benzoyl chloride (5 g) in dioxane (100 ml) over a period of 1 hour. The reaction mixture was then stirred for a further 2 hours. Water (100 ml) was then added to the reaction mixture and unwanted organics were extracted into ethyl acetate (5×100 ml). Hydrochloric acid (5N) was then added to the aqueous layer and the free acid was extracted into ethyl acetate (250 ml), dried (MgSO$_4$) and solvent was removed in vacuo to afford a pale brown solid. A portion of this solid (0.5 g) was added to a solution of caesium carbonate (0.26 g) in methanol (20 ml). Once a clear solution was obtained, the solvent was removed in vacuo to leave a white solid. Dimethylformamide (20 ml) was added to the residue, then 2-trifluoromethylbenzylbromide (0.17 g) was added and the reaction was stirred for 16 hours at ambient temperature. The solvent was removed in vacuo, the residue was dissolved in dichloromethane (100 ml) and washed with water (2×50 ml), and dried (MgSO$_4$). The solvent was removed in vacuo to afford a white solid. The product was purified by recrystallisation from ethyl acetate/petroleum ether to give the title compound (0.58 g), m.p. 117° C. $^1$H NMR (360 MHz, CDCl$_3$) δ8.06 (1H, s), 7.66 (2H, d, J=7.2 Hz), 7.57–7.33 (9H, m), 7.16 (1H, t, J=7.2 Hz), 7.06 (1H, t, J=7.2 Hz), 6.92 (1H, d, J=2.1 Hz), 6.66 (1H, d, J=7.2 Hz), 5.35 (1H, d, J=14.4 Hz), 5.30 (1H, d, J=14.4 Hz), 5.22 (1H, m), 3.46 (2H, d, J=7.2 Hz).

EXAMPLE 13

3-Trifluoromethylbenzyl 3-(3-indolyl)-2-benzamidopropionate

Following the method of Example 12, 3-trifluoromethyl benzybromide gave the title compound, mp 118° C. $^1$H NMR (360 MHz, CDCl$_3$) δ8.01 (1H, s), 7.66 (2H, d, J=7.2 Hz), 7.59–7.33 (9H, m), 7.16 (1H, t, J=7.2 Hz), 6.65 (1H, d, J=2.2 Hz), 6.66 (1H, d, J=7.2 Hz), 5.19 (1H, m), 5.13 (2H, s), 3.44 (2H, d, J=7.2 Hz).

EXAMPLE 14

4-Chlorobenzyl 3-(3-indolyl)-2-benzamidopropionate

Following the method of Example 10, 4-chlorobenzylchloride gave the title compound, m.p. 119° C. $^1$H NMR (360 MHz, CDCl$_3$) δ8.01 (1H, s), 7.67 (2H, d, J=7.2 Hz), 7.54–7.04 (1H, m), 6.62 (1H, d, J=2.5 Hz), 6.65 (1H, d, J=7.2 Hz), 5.17 (1H, m), 5.07 (2H, m), 3.43 (2H, d, J=7.2 Hz).

EXAMPLE 15

3,5-Bistrifluoromethylbenzyl 2-acetamido-3-(3-indolyl)propionate

Following the method of Example 1, 3,5-bistrifluoromethylbenzyl bromide (6.16 g) and N acetyl-L-tryptophan (4.92 g) gave the title compound which was recrystallised from ethyl acetate/petroleum ether (3.7 g), m.p. 147°–148° C. $^1$H NMR (360 MHz, CDCl$_3$) δ8.01 (1H, s), 7.83 (1H, s), 7.61 (1H, s), 7.51 (1H, d, J=8 Hz), 7.32 (1H, d, J=8 Hz), 7.17 (1H, t, J=7 Hz), 7.09 (1H, t, J=7 Hz), 6.91 (1H, d, J=2 Hz), 5.98 (1H, s), 5.13 (1H, d, J=13 Hz), 5.06 (1H, t, J=13 Hz), 4.96 (1H, t, J=6 Hz), 3.31 (2H, m), 1.98 (1H, s); Found: C, 56.08; H, 3.79; N, 5.74. C$_{22}$H$_{18}$N$_2$F$_6$O$_3$ requires C, 55.84; H, 3.84; N, 5.93%.

EXAMPLE 16

3,5-Dimethylbenzyl 2-(3-methylureido)-3-(3-indolyl)propionate 3,5-Dimethylbenzyl 2-amino-3-(3-indolyl)propionate hydrochloride (1.0 g) was suspended in tetrahydrofuran (10 ml). Triethylamine (0.38 ml) was added and the solution was stirred at room temperature for 15 minutes. Methyl isocyanate (0.19 ml) was added and the solution was stirred for 1 hour. The tetrahydrofuran was removed in vacuo and the residue was taken up in ethyl acetate. The organic phase was washed with dilute hydrochloric acid, water and sodium bicarbonate solution. The organic extract was dried (Na$_2$SO$_4$) and evaporated. The residual solid was recrystallised from ethyl acetate/petroleum ether to yield the title compound, (1.17 g), m.p. 66°–68° C. $^1$H NMR (360 MHz, CDCl$_3$) δ7.99 (1H, s), 7.52 (1H, d, J=8 Hz), 7.30 (1H, d, J=8 Hz), 7.16 (1H, t, J=8 Hz), 7.08 (1H, t, J=8 Hz), 6.96 (1H, s), 6.88 (2H, s), 6.76 (1H, s), 5.01 (2H, s), 4.83 (1H, m), 3.26 (2H, d, J=5 Hz), 2.65 (3H, s), 2.30 (6H, s). Found: C, 68.64; H, 6.36; N, 10.86. C$_{22}$H$_{25}$O$_3$N$_3$. 0.3(H$_2$O) requires C, 68.57; H, 6.66; N, 10.90.

EXAMPLE 17

3,5-Dimethylbenzyl 2-ureido-3-(3-indolyl)propionate

Following the method of Example 16, 3,5-dimethylbenzyl 2-amino-3-(3-indolyl)propionate hydrochloride and trimethylsilyl isocyanate gave the title compound after recrystallisation from ethyl acetate/petroleum ether, m.p. 154°–156° C. (dec.). $^1$H NMR (360 MHz, CDCl$_3$) δ7.99 (1H, s), 7.52 (1H, d, J=8 Hz), 7.30 (1H, d, J=8 Hz), 7.16 (1H, t. J=8 Hz), 7.08 (1H, t, J=8 Hz), 6.97 (1H, s), 6.88 (2H, s), 6.77 (1H, s), 5.21 (1H, d, J=8 Hz), 5.01 (2H, s), 4.85 (1H, m), 4.34 (2H, s), 3.28 (2H, J=5 Hz), 2.30 (6H, s).

EXAMPLE 18

3,5-Dimethylbenzyl 2-benzenesulphonamido-3-(3-indolyl)propionate 3,5-Dimethylbenzyl 2-amino-3-(3-indolyl)propionate hydrochloride (1.0 g) was suspended in tetrahydrofuran (10 ml). Triethylamine (0.38 ml) was added and the solution was stirred for 15 mins. Benzenesulphonyl chloride (0.35 ml) was added and the solution was stirred at room temperature for 1 hour. Work-up as for Example 14 gave a solid which was recrystallised from ethanol to yield the title compound, 0.85 g, m.p. 114°–116° C. $^1$H NMR (360 MHz, CDCl$_3$) δ7.98 (1H, s), 7.72 (2H, d, J=7 Hz), 7.54–7.30 (5H, m), 7.17 (1H, t, J=7 Hz), 7.06 (1H, t. J=7 Hz), 6.94 (1H, s), 6.89 (1H, s), 6.62 (2H, s), 5.17 (1H, d, J=9.2 Hz), 4.68 (2H, AB$_q$, J=11.9 Hz), 4.33 (1H, m), 3.27 (2H, m), 2.27 (6H, s).

EXAMPLE 19

3,5-Dimethylbenzyl 2-methanesulphonamido-3-(3-indolyl)propionate

Following the method of Example 18, 3,5-dimethylbenzyl 2-amino-3-(3-indolyl)propionate hydrochloride and methanesulphonylchloride gave the title compound which was recrystallised from ethyl acetate/petroleum ether, m.p. 96°–97° C. $^1$H NMR (360 MHz, CDCl$_3$) δ8.18 (1H, s), 7.70 (1H, d, J=7 Hz), 7.48 (1H, d, J=7 Hz), 7.37 (1H, t, J=7 Hz), 7.28 (1H, t, J=7 Hz), 7.12 (1H, s), 7.08 (1H, s), 6.98 (2H, s), 5.04 (2H, s), 4.89 (1H, d, J=9.2 Hz), 4.50 (1H, m), 3.32 (2H, d, J=5.7 Hz), 2.72 (3H, s), 2.30 (6H, s). Found: C, 62.6; H, 5.9; N, 6.8. C$_{21}$H$_{24}$N$_2$O$_4$S requires C, 63.0; H, 6.0; N, 7.0.

EXAMPLE 20

3,5-Dimethylbenzyl 2-methoxycarbonylamino-3-(3-indolyl)propionate

Following the method of Example 18, 3,5-dimethylbenzyl 2-amino-3-(3-indolyl)propionate hydrochloride and methyl chloroformate gave the title compound after recrystallisation from ethyl acetate/petroleum ether, m.p. 128°–129° C. $^1$H NMR (360 MHz, CDCl$_3$) δ8.04 (1H, s), 7.52 (1H, d, J=8.0 Hz), 7.32 (1H, d, J=8 Hz), 7.18 (1H, t, J=8 Hz), 7.09 (1H, t, J=8 Hz), 6.95 (1H, s), 6.83 (2H, s), 5.25 (1H, d, J=7.5 Hz), 5.00 (2H, dd, J=12 Hz), 4.73 (1H, m), 3.65 (3H, s), 3.29 (2H, d, J=5 Hz), 2.29 (6H, s).

EXAMPLE 21

3,5-Dimethylbenzyl 2-ethylallophanato-3-(3-indolyl)propionate

Following the method of Example 18, 3,5-dimethylbenzyl 2-amino-3-(3-indolyl)propionate hydrochloride and ethoxycarbonyl isocyanate gave the title compound after purification by chromatography on silica gel (ethyl acetate), m.p. 57°–59° C. $^1$H NMR (360 MHz, CDCl$_3$) δ8.32 (1H, d, J=7.5 Hz), 8.01 (1H, s), 7.55 (1H, d, J=8 Hz), 7.32 (1H, d, J=8 Hz), 7.17 (1H, t, J=7 Hz), 7.08 (2H, m), 6.97 (1H, s), 6.94 (1H, s), 6.84 (2H, s).

EXAMPLE 22

3,5-Dimethylbenzyl-3-(3-indolyl)-2-(2,4-dichlorobenzamido)propionate

Following the method of Example 12, 2,4-dichlorobenzoyl chloride and L-tryptophan gave the title compound after recrystallisation from ethyl acetate/petroleum ether, m.p. 125°–126° C. $^1$H NMR (360 MHz, CDCl$_3$) δ8.01 (1H, s), 7.54 (1H, d, J=7 Hz), 7.49 (1H, d, J=7 Hz), 7.35–6.77 (9H, m), 5.15 (1H, m), 5.05 (2H, s), 3.44 (2H, m), 2.30 (6H, s).

EXAMPLE 23

3,5-Dimethylbenzyl-3-(3-indolyl)-2-methyl-2-benzamidopropionate

Following the method of Example 12, D,L-α-methyl tryptophan was treated with benzoyl chloride followed by 3,5-dimethylbenzyl bromide to give the title compound after recrystallisation from ethyl acetate/petroleum ether, m.p. 73°–74° C. $^1$H NMR (CDCl$_3$) δ7.99 (1H, s), 7.64–6.65 (13H, m), 5.10 (1H, d, J=7 Hz), 5.01 (1H, d, J=7 Hz), 3.76 (1H, d, J=7 Hz), 3.51 (1H, d, J=7 Hz), 2.27 (6H, s), 1.66 (3H, s).

EXAMPLE 24

3,5-Dimethylbenzyl 2-acetamido-3-(3,4-dichlorophenyl)propionate a) Ethyl-2-acetamido-2-carbethoxy-3-(3,4-dichlorophenyl)propionate Sodium pellets were dissolved in ethanol (200 ml). Diethyl acetamidomalonate (6.53 g) was added and the solution stirred for 30 minutes. 3,4-Dichlorobenzyl bromide (10.0 g), was added and the solution refluxed for 3.5 hours. The solution was filtered whilst hot and allowed to cool before water (200 ml) was added. On standing at 4° C. for 12 hours the title compound precipitated as colourless crystals which were removed by filtration and dried under vacuum (9.27 g). $^1$H NMR (360 MHz, CDCl$_3$) δ7.32 (1H, d, J=8 Hz), 7.10 (1H, d, J=2 Hz), 6.85 (1H, dd, J=8, 2 Hz), 6.55 (1H, s), 4.28 (2H, m), 3.62 (2H, s), 2.05 (3H, s), 1.3 (3H, t, J=7 Hz).

b) 3,5-Dimethylbenzyl 2-acetamido-3-(3,4-dichlorophenyl)propionate

The product of part a) was dissolved in ethanol (100 ml) and stirred for 1 hour with aqueous sodium hydroxide. the mixture was diluted with water (100 ml), adjusted to pH1 with 2N hydrochloric acid and the resulting precipitate removed by filtration and dried under vacuum. This was then dissolved in 1,4-dioxan (100 ml) and the solution heated under reflux for 12 hours after which the solvent was removed in vacuo and the residue dissolved in ethyl acetate then washed with saturated sodium bicarbonate solution, water and brine. The organic fractions were dried (MgSO$_4$) and the solvent removed in vacuo to give an oil which crystallised on standing. This crystalline material was dissolved in tetrahydrofuran (50 ml) and stirred with an equal volume of 2N lithium hydroxide solution for 1 hour. The mixture was adjusted to pH1 with 2N hydrochloric acid and the solution extracted with ethyl acetate. The organic fractions were dried (MgSO$_4$) and the solvent removed in vacuo. The resulting oil was treated according to the method of Example 1 using cesium carbonate (2.09 g) and 3,5-dimethyl benzylbromide (1.53 g) to give, after purification by column chromatography and trituration with diethyl ether, the title compound as a white solid (1.17 g), m.p. 118°–119° C. $^1$H NMR (360 MHz, CDCl$_3$) δ7.24 (1H, d, J=8 Hz), 7.12 (1H, d, J=2 Hz), 7.00 (1H, s), 6.91 (1H, s), 6.80 (1H, dd, J=8, 2 Hz), 6.01 (1H, d, J=7 Hz), 5.06 (2H, dd, J=12, 12 Hz), 4.89 (1H, m), 3.07 (2H, m), 2.33 (6H, s), 2.00 (3H, s). Found: C, 61.06; H, 5.43; N, 3.54 C$_{20}$H$_{21}$C$_{12}$NO$_3$ requires C, 60.92; H, 5.37; N, 3.55%.

EXAMPLE 25

N-(3,5-Dimethylbenzyl)-2-benzamido-3-(3-indolyl)propionamide

N-α-Benzoyl tryptophan (0.67 g) was dissolved in dry dimethylformamide (15 ml). The solution was cooled to 0° C. and 1-hydroxybenzotriazole (0.3 g), followed by 1-(3-dimethylaminopropyl)-3-ethylcarbodiimide hydrochloride (0.433 g) was added. The reaction was stirred for 0.5 hours and then 3,5-dimethylbenzylamine (0.3 g) was added and the reaction was stirred for 16 hours. The reaction was filtered, diluted with dichloromethane (500 ml), and washed with saturated sodium bicarbonate solution (100 ml), brine (100 ml) and water (100 ml). The separated organic phase was dried (MgSO$_4$), filtered and evaporated to yield an oil which was purified by chromatography on silica using dichloromethane/methanol (98:2) to give the title compound as a white solid (0.23 g); m.p. 177°–178° C. Found: C, 76,28; H, 6.46; N, 9.85. C$_{27}$H$_{27}$N$_3$O$_2$ requires C, 76.21; H, 6.40; N, 9.87%.

EXAMPLE 26

N-(3,5-Bistrifuoromethylbenzyl)-2-benzamido-3-(3-indolyl)propionamide a) N-(3,5-Bistrifluoromethylbenzyl)-2-amino-3-(3-indolyl)propionamide Hydrochloride N-α-BOC-L-Tryptophan (12.6 g) and triethylamine (8.36 g) were dissolved in dichloromethane, cooled to –10° C., and treated with isobutylchloroformate. The reaction was stirred for 15 minutes before adding 3,5 bistrifluoromethylbenzylamine (10 g), and stirring for 30 minutes at 0° C. The solvent was removed and the residue was taken up into ethyl acetate and washed with 10% citric acid (100 ml), saturated sodium bicarbonate solution (100 ml) and water (100 ml). The organic phase was dried (MgSO$_4$) filtered and evaporated. The residue was dissolved in methanolic hydrogen chloride and stirred 48 hours. The solvent was removed to yield the title compound (14.11 g).

b) N-(3,5-Bistrifluoromethylbenzyl)-2-benzamido-3-(3-indolyl)propionamide

The product of part a) (1.02 g) was dissolved in a mixture of pyridine (50 ml) and benzoyl chloride (0.31 g) and stirred for 18 hours. The reaction mixture was poured onto ice, acidified with hydrochloric acid (2M) and extracted with ethyl acetate. The organic phase was washed with brine, saturated sodium bicarbonate and brine, dried (MgSO$_4$), filtered, and evaporated to yield the title compound as a white solid (0.2 g), m.p. 182°–184° C. Found: C, 60.90; H, 4.10; N, 8.10; C$_{27}$H$_{21}$F$_6$N$_3$O$_2$ requires C, 60.79, H, 3.97; N, 7.88%.

EXAMPLE 27

N-(3,5-Dimethylbenzyl)-N-methyl-2-benzamido-3-(3-indolyl)propionamide a) 3,5-Dimethyl-N-methylbenzylamine N-$^t$Butyloxycarbonyl-3,5-dimethylbenzylamine (0.95 g) was treated with sodium hydride (0.16 g of a 60% dispersion in oil) in dry tetrahydrofuran. The reaction was stirred for 10 minutes before adding iodomethane (1 ml) and stirring for 16 hours. The solvent was removed and the residue was partitioned between ethyl acetate and water. The organic phase was dried (MgSO$_4$), filtered and evaporated to yield a white solid, which was dissolved in methanolic hydrogen chloride and heated to reflux for 30 minutes. The solvent was removed by evaporation and the residue was partitioned between 2N sodium hydroxide and ethyl acetate. The organic phase was dried (MgSO$_4$) and evaporated to yield the crude title product (0.28 g).

b) N-(3,5-Dimethylbenzyl)-N-methyl-2-benzamido-3-(3-indolyl)propionamide

Following the method of Example 25, N-α-benzoyl tryptophan and 3,5-dimethyl-N-methylbenzylamine gave the title compound, m.p. 140°–142° C. Found: C, 76.90; H, 6.78, N, 9.53 C$_{28}$H$_{29}$N$_3$O$_2$ requires C, 76.51; H, 6.65; N, 9.56%.

EXAMPLE 28

1-(3,5-Dimethylbenzyloxy)-2-amino-3-(3-indolyl)propane Hydrogen Oxalate a) 2-Amino-3-(3-indolyl)-1-propanol L Tryptophan (10.2 g) was cautiously added in portions to a stirred solution of lithium aluminium hydride in tetrahydrofuran (1M, 150 ml). The reaction was stirred for 72 hours and then heated to reflux for 1 hour. The reaction mixture was cooled and then quenched carefully with 2N sodium hydroxide (150 ml). Ethyl acetate (500 ml) was added and the mixture was filtered through a pad of Celite. The organic phase was washed with water, dried (MgSO$_4$) and evaporated to yield the crude title compound.

b) 2-t-Butyloxycarbonylamino-3-(1-t-butyloxycarbonyl-3-indolyl)-1-propanol. The product of part a) (4.6 g) was dissolved in acetonitrile and treated wth 4-dimethylaminopyridine (2.95 g) followed by di-t-butyl dicarbonate (72.6 g) at 0° C. The reaction was stirred for two hours, and the solvent removed by evaporation. The residue was dissolved in methanol (500 ml), potassium hydroxide (1.3 g) was added, and the reaction was stirred for one hour before the solvent was removed and the residue partitioned between ethyl acetate and water. The organic phase was dried (MgSO$_4$), evaporated, and the residue purified by column chromatography using ethyl acetate/petroleum ethereum ether (1:4) to yield the title compound.

c) 1-(3,5-Dimethylbenzyloxy)-2-amino-3-(3-indolyl)propane Hydrogen Oxalate

The product of part b) (5.7 g) was dissolved in dimethyl formamide (10 ml) and tetrahydrofuran (40 ml) and treated with sodium hydride (80% dispersion in oil, 0.438 g) and stirred for 15 minutes before adding 3,5-dimethylbenzyl bromide (2.9 g). The reaction was stirred for 16 hours before removing the solvent and partitioning between ethyl acetate and water. The organic phase was dried (MgSO$_4$) and evaporated to give a residue which was purified by column chromatography on silica using ethyl acetate/petroleum ethereum ether (1:4). The resulting oil was dissolved in methanolic hydrogen chloride and stirred for 16 hours. The solvent was removed and the residue partitioned between ethyl acetate and potassium carbonate solution. The organic phase was dried (MgSO$_4$), filtered, and evaporated. The residue was purified by column chromatography using dichloromethane/methanol (9:1) to yield an oil which was treated with ethereal oxalic acid to yield the title compound as a white solid (0.150 g). $^1$H NMR (360 MHz D$_6$ DMSO) δ11.04 (1H, s), 7.56 (1H, d, J=8 Hz), 7.37 (1H, d, J=7 Hz), 7.00 (1H, t, J=7 Hz), 6.93 (2H, s), 6.90 (1H, s), 4.43 (1H, d, J=12 Hz), 4.36 (1H, d, J=12 Hz), 3.54–3.42 (3H, m), 3.09–2.96 (2H, m) 2.24 (6H, s). Found: C, 66.04; H, 6.55; N, 6.98. C$_{20}$H$_{24}$N$_2$O (COOH)$_2$ requires C, 66.32; H, 6.58; N, 7.03%.

EXAMPLE 29

1-(3,5-Dimethylbenzyloxy)-2-acetamido-3-(3-indolyl)propane

The compound of Example 28 was treated in the same manner as Example 4b to yield the title compound as a white solid. $^1$H NMR (360 MHz, CDCl$_3$) δ8.05 (1H, s), 7.72 (1H, d, J=8 Hz), 7.34 (1H, d, J=8 Hz), 7.19 (1H, t, J=7 Hz), 7.12, (1H, t, J=7 Hz), 6.96 (4H, s), 5.85 (d, J=8 Hz), 4.44–4.36 (1H, m), 3.48–3.38 (2H, m), 3.11–2.99 (2H, m), 2.33 (6H, s), 1.94 (3H, s). Found: C, 74.86; H, 7.56; N, 7.74. C$_{22}$H$_{26}$N$_2$O$_2$0.2(H$_2$O) requires C, 74.63; H, 7.51; N, 7.91%.

EXAMPLE 30

N-(3,5-Bistrifluoromethylbenzyl)-3-(3-indolyl)-2-(3-methylureido)propionamide Triethylamine (0.3 ml) was added to a stirred solution of the compound of Example 26 (1 g) in tetrahydrofuran (15 ml), at room temperature under a nitrogen atmosphere. After 5 minutes methyl isocyanate (0.13 ml) was added and the solution was stirred for 3 hours. The solvent was removed and the residue was dissolved in ethyl acetate (50 ml). The solution was washed with dilute hydrochloric acid, water and sodium bicarbonate solution. After drying over Na$_2$SO$_4$ removal of the solvent gave the title compound (0.9 g) after recrystallisation from ethyl acetate/petroleum ethereum ether, m.p. 213°–215° C. Found: C, 54.62; H, 4.28; N, 11.41. C$_{22}$H$_{20}$N$_4$O$_2$F$_6$ requires C, 54.32; H, 4.14; N, 11.51.

EXAMPLE 31

N-(3,5-Bistrifluoromethylbenzyl)-3-(3-indolyl)-2-(3-phenylureido)propionamide Prepared by the method of Example 30 using phenyl isocyanate, m.p. 219°–221° C. Found: C, 58.06; H, 4.12; N, 9.94. C$_{27}$H$_{22}$N$_4$O$_2$F$_6$ requires C, 58.17; H, 4.15; N, 10.05.

EXAMPLE 32

N-(3,5-Bistrifluoromethylbenzyl)-3-(3-indolyl)-2-ureidopropionamide

Prepared by the method of Example 30 using trimethylsilylisocyanate, m.p. 210°–212° C. Found: C, 53.63; H, 3.91; N, 11.50. C$_{21}$H$_{18}$N$_4$O$_2$F$_6$ requires C, 53.39; H, 3.84; N, 11.86.

EXAMPLE 33

3-(3-Benzo[b]thienyl)-2-acetamido-1-(3,5-bis trifluoromethylbenzyloxy)propane a) 3-(3-Benzo[b]thienyl)-2-amino-1-propanol A solution of β-(3-benzo[b]thienyl)DL alanine (5.0 g) [P. N. Rao et al, *Int. J. Peptide Protein Res*, 29, 118, (1987)] in dry tetrahydrofuran (50 ml) was added to an ice cold solution of lithium aluminium hydride in dry tetrahydrofuran (22 ml of a 1M solution). Once addition was complete the mixture was warmed to reflux for one hour, cooled to room temperature and the reaction quenched by the addition of 4N sodium hydroxide (5.0 ml). The reaction mixture was diluted with water (100 ml) extracted with ethyl acetate (2×100 ml), the organic layers were separated, dried (MgSO$_4$), filtered and the solvent removal under reduced pressure to afford the title compound as a colourless oil. $^1$H NMR (360 MHz, CDCl$_3$) δ2.65 (1H, m, CH$_2$CHCH$_2$OH), 2.99 (2H, m, CH$_2$CH$_2$OH), 3.23 (2H, m, CH$_2$CHCH$_2$OH), 7.44 (2H, m, 2×ArH), 7.61 (1H, s, S-CHC), 7.86 (1H, dd, J=6.0, 1.0 Hz, ArH), 7.97 (1H, dd, J=6.0, 1.0 Hz, ArH). m/z (EI$^+$) 207.

b) 3-(3-Benzo[b]thienyl)-2-t-butyloxycarbonylamino-1-propanol

Di-tert-butyldicarbonate (3.6 g) was added to a stirred solution of the product of part a) (3.5 g) in dry dichloromethane (100 ml). The resulting solution was stirred at room temperature for 18 hours. The solvent was removed under reduced pressure and the residue subjected to flash chromatography on silica gel using ethyl acetate/n-hexane (1:1) as eluent. The product was recovered as a colourless oil. $^1$H NMR (360 MHz, CDCl$_3$) δ1.42 (9H, s, C (CH$_3$)$_3$), 3.10 (2H, m, CH$_2$CHCH$_2$OH), 3.63 (2H, m, CH$_2$CHCH$_2$OH), 4.09 (1H, m, CH$_2$CHCH$_2$OH), 4.82 (1H, bs, NH), 7.20 (1H, s, S-CH=C), 7.37 (2H, m, 2×ArH), 7.85 (2H, m, 2×ArH). m/z (EI$^+$)307.

c) 3-(3-Benzo[b]thienyl)-2-t-butyloxycarbonylamino-1-(3, 5-bistrifluoromethylbenzyloxy)propane Sodium hydride (162 mg of a 60% dispersion in oil) was added to a solution of the product of part b) (2.08 g) in dry dimethylformamide (10 ml) at −10° C. The solution was stirred at −10° C. for 15 minutes and 3,5-bistrifluoromethylbenzyl bromide (1.30 ml) was added. Stirring was continued at −10° C. for 30 minutes and at room temperature for a further 4 hours. The reaction was quenched by the addition of saturated ammonium chloride solution (10 ml). The reaction was diluted with water (100 ml) and extracted into ethyl acetate (2×50 ml). The organic layers were separated, dried over MgSO$_4$, filtered and the solvent removed under reduced pressure. The residue was purified by flash chromatography in silica gel using ethyl acetate/n-hexane (1.5:1) as eluent. The title compound was recovered as an oil. $^1$H NMR (360 MHz, CDCl$_3$) δ1.43 (9H, s, C(CH$_3$)$_3$), 3.15 (2H, m, $_2$CHCH$_2$OR, 3.49 (2H, m, CH$_2$CHCH$_2$OCH$_2$R), 4.11 (1H, bm, CH$_2$CHCH$_2$OCH$_2$R), 4.59 (2H, m, OCH$_2$Ar), 4.89 (1H, bs, NH), 7.15 (1H, s, SCH=C), 7.37 (2H, m, 2×ArH), 7.76 (3H, bs, CF$_3$C-C̲H̲-CCF$_3$ and 2×CF$_3$C-C̲H̲-CCH $_2$), 7.83 (2H, m, 2×ArH). m/z (EI$^+$)533.

d) 3-(3-Benzo[b]thienyl)-2-amino-1-(3,5-bistrifluoromethylbenzyloxy)propane Hydrochloride Hydrogen chloride gas was bubbled through a solution of the product of part c) (2.0 g) in dry methanol (100 ml) at 0° C. for 3 hours. The solvent was then removed under reduced pressure to afford a white solid. Recrystallisation of the crude product from ethanol afforded the title compound as white needles, m.p. 196°–98° C. $^1$H NMR (360 MHz, D$_6$ DMSO) δ2.40 (1H, m, CH$_2$C̲H̲CH$_2$O) 3.24 (2H, m, CH$_2$CH C̲H̲$_2$O), 3.61 (2H, m, C̲H̲$_2$CHCH$_2$O), 4.71 (2H, m, O C̲H̲$_2$Ar), 7.39 (2H, m, 2×ArH), 7.62 (1H, s, S CM=C), 7.89 (2H, m, 2×ArH), 7.92 (1H, s, CF$_3$-CH-CCF$_3$), 8.01 (2H, s, CF$_3$C-C̲H̲-C-CH$_2$) m/z (EI$^+$) 434.

e) 3-(3-Benzo[b]thienyl)-2-acetamido-1-(3,5-bistrifluoromethylbenzylory)propane

Acetyl chloride (0.15 ml) was added dropwise to a solution of the product of part d) (730 mg) and triethylamine (0.3 ml) in dry dichloromethane (50 ml). The resulting mixture was allowed to stir at room temperature for 4 hours. The reaction was then diluted with water and the organic layer separated, dried (MgSO$_4$), filtered and the solvent removed under reduced pressure. Recrystallisation from n-hexane afforded the title compound as white needles, m.p. 97°–98° C. $^1$H NMR (360 MHz, D$_6$ DMSO) δ1.78 (3H, s, NCOC̲H̲$_3$), 2.96 (2H, m, CH$_2$CHC̲H̲$_2$O), 3.40 (2H, m, C̲H̲$_2$CHCH$_2$O), 4.27 (1H, m, CH$_2$C̲H̲CH$_2$O), 4.64 (2H, m, O C̲H̲$_2$Ar), 7.37 (2H, m, 2×ArH), 7.95 (2H, m, 2×ArH), 7.99 (3H, bs, CF$_3$-C̲H̲-CCF$_3$ and 2×CF$_3$C-CH$_2$). m/z (EI$^+$) 475. Found: C, 55.57; H, 4.10; N, 2.96. C$_{22}$H$_{19}$NO$_2$SF$_6$ requires C, 55.46; H, 4.03; N, 2.95%.

EXAMPLE 34

(2S)-2-Amino-1-(3,5-dimethylbenzyloxy)-3-phenylpropane Hemi Hydrogen Oxalate a) (2S)-2-t-Butyloxycarbonylamino-3-phenyl-1-propanol To a solution of L-Phenylalaninol (3.52 g) in dichloromethane (35 ml) was added di-t-butyldicarbonate (5.09 g). After 16h the solvent was removed in vacuo and the residue chromatographed on silica gel (eluting with 10–20% ethyl acetate in petroleum ether to give the title compound.

b) (2S)-2-t-Butyloxycarbonylamino-1-(3,5-dimethylbenzyloxy)-3-phenylpronane

To a cooled (0° C.) solution of the product of part a) (1.50 g) in tetrahydrofuran (8 ml) and dimethylformamide (2 ml) was added sodium hydride (0.18 g, 80% suspension in oil). After the effervescence had ceased, 3,5-dimethylbenzyl bromide (1.18 g) was added for 16 hours. The solvent was removed in vacuo and a solution of the residue in dichloromethane was washed with water and dried (MgSO$_4$). After removal of the solvent in vacuo, the residue was chromatographed on silica gel (eluting with 10% and 20% ethyl acetate in petroleum ether) to give the title compound as an oil.

c) (2S)-2-Amino-1-(3,5-dimethylbenzyloxy)-3-phenylpropane Hemi Hydrogen Oxalate

The product of part b) (0.564 g) was dissolved in trifluoroacetic acid (5 ml) for 40 minutes followed by evaporation in vacuo. The residual oil was dissolved in ethanol and oxalic acid (0.138 g) added. On addition of diethyl ether crystals formed to give the title compound, mp=135°–137° C., m/e (CI$^+$) 270 (M+H), (CI$^-$) 268 (M-H). Found: C, 71.82; H, 7.48; N, 4.46: C$_{18}$H$_{23}$NO 0.55(C$_2$H$_2$O$_4$) requires C, 71.94; H, 7.62; N, 4.39%.

EXAMPLE 35

(2S)-2-Acetamido-1-(3,5-dimethylbenzyloxy)-3-phenylpropane

To a solution of L-phenylalaninol (1.2 g) in CH$_2$Cl$_2$ (10 ml) was added acetic anhydride (0.75 ml). After 16h the solution was evaporated to dryness. To a solution of the residue dissolved in tetrahydrofuran (7 ml) and dimethylformamide (2 ml) was added sodium hydride (0.155 g, 80% suspension in oil). After 10 minutes 3,5-dimethylbenzyl bromide (1.03 g) was added and the solution stirred at room temperature for 16 hours. After removal of the solvent in vacuo the residue was dissolved in dichloromethane and this solution was washed with water, saturated brine and dried (MgSO$_4$). The solvent was removed in vacuo and the residue chromatographed on silica gel (eluting with 0 to 50% ethyl acetate in petroleum ether) to give the title compound as a crystalline solid, mp=76°–78° C., m/e (CI$^+$) 312 (M+H), (CI$^{31}$ ) 310 (M-H). Found: C, 76.82; H, 8.11; N, 4.44. C$_{20}$H$_{25}$NO$_2$.0.05(CH$_3$COOC$_2$H$_5$) requires C, 76.78; H, 8.07; N, 4.45%.

EXAMPLE 36

2-Amino-1-(3,5-dimethylbenzyloxy)-3-(1-naphthyl)propane, Acetic Acid Salt

The title compound was prepared from (D/L)-3-(1-naphthyl)alaninol in an analogous manner to that described in Example 34, mp 101°–103° C. $^1$H NMR (360 MHz, CDCl$_3$); δ1.45 (9H, bs), 2.37 (6H, s), 3.31–3.38 (4H, m), 4.10 (1H, bs), 4.35–4.43 (2H, m), 5.10 (1H, bs), 6.69 (3H, s), 7.26–7.36 (2H, m), 7.45–7.53 (2H, m), 7.71–7.73 (1H, m), 7.82–7.84 (1H, m), 8.30 (1H, m). Found: C, 79.03; H, 7.56; N, 4.11%: C$_{22}$H$_{25}$NO.0.5(C$_2$H$_4$O$_2$) requires C, 79.05; H, 7.79; N, 4.01%.

EXAMPLE 37

2-Acetamido-1-(3,5-dimethylbenzyloxy)-3-(1naphthyl)propane

Acetic anhydride (0.2 ml) was added to a solution of the compound of Example 36 (0.36 g) in pyridine (5 ml). After 16h the solution was partitioned between 1M HCl and ethyl acetate. After drying the organic phase (MgSO$_4$) the solvent was removed in vacuo and the residue crystallized from diethyl ether to give the title compound, mp 119°–120° C. $^1$H NMR (360 MHz, CDCl$_3$) δ1.99 (3H, s), 2.34 (6H, s), 3.20–3.27 (1H, m), 3.31–3.37 (2H, m), 3.46–3.51 (1H, m), 4.37–4.45 (3H, m), 6.03–6.05 (1H, m), 6.97 (3H, s), 7.24–7.26 (1H, m), 7.26–7.35 (1H, m), 7.45–7.49 (1H, m), 7.53–7.57 (1H, m), 7.71–7.73 (1H, m), 7.02–7.04 (1H, m), 8.41–8.43 (1H, m). Found: C, 79.63; H, 7.69; N, 3.93: C$_{24}$H$_{27}$NO$_2$ requires C, 79.74; H, 7.53; N, 3.87%.

EXAMPLE 38

2-Amino-1-(3,5-dimethylbenzyloxy)-3-(2-naphthyl)propane Hydrogen Oxalate

The title compound was prepared from (D/L)-3-(2-naphthyl)alaninol in an analogous manner to that described in Example 34, mp 173°–175° C. $^1$H NMR (360 MHz, DMSO d$_6$) δ 2.20 (6H, s), 3.00–3.2 (2H, m), 2.4–2.6 (2H, m), 2.6–2.8 (1H, m), 4.3–4.5 (2H, m), 6.91 (1H, s), 6.93 (2H, s), 7.4 (1H, m), 7.5–7.6 (2H, m), 7.73 (1H, s), 7.8–8.0 (3H, m).

Found: C, 70.04; H, 6.79; N, 3.35: $C_{22}H_{25}NO \cdot C_2H_2O_4$ requires C, 70.39; H, 6.65; N, 3.42%.

EXAMPLE 39

3,5-Dimethylbenzyl 2-(N,N-diethylamino)-3-(3-indolyl)propionate Hydrochloride Following the method of Example 7, 3,5-dimethylbenzyl-2-amino-3-(3-indolyl)propionate hydrochloride (500 mg) was treated with acetaldehyde (154 mg) and sodium cyanoborohydride (220 mg) to give the title compound after recrystallisation from ethyl acetate (230 mg); mp 184°–185° C.; Found: C, 68.71; H, 7.57; N, 6.67. $C_{24}H_{30}N_2O_2 \cdot HCl \cdot 0.5(H_2O)$ requires C, 68.71; H, 7.65; N, 6.60%.

EXAMPLE 40

3,5-Bistrifluoromethylbenzyl 3-(3-indolyl)-2-benzamido propionate a) 3,5-Bistrifluoromethylbenzyl 2-(1,1-dimethylethoxycarbonylamino)-3-(3-indolyl)propionate Following the method of Example 1, 3,5-bistrifluoromethylbenzyl bromide (4.9 g) and N α BOC-L-tryptophan (5 g) gave the title compound after recrystallisation from ethyl acetate/petroleum ether.

b) 3,5-Bistrifluoromethylbenzyl 2-amino-3-(3-indolyl)propionate Hydrochloride

The title compound (3.0 g) was prepared from the product of the preceding preparation by the method of Example 4a.

c) 3,5-Bistrifluoromethylbenzyl 3-(3-indolyl)-2-benzamido propionate

Following the method of Example 4b the preceding compound (1.5 g) and benzoyl chloride (0.41 ml) gave the title compound after purification by column chromatography on silica using ethyl acetate/petroleum ether (0.68 g); mp 162°–164° C.; Found: C, 59.69; H, 3.82; N, 5.02. $C_{26}H_{19}F_6N_2O_3$ requires C, 59.89; H, 3.67; N, 5.37%.

EXAMPLE 41

3,5-Bistrifluoromethylbenzyl 2-(N,N-dimethylamino)-3-(3-indolyl)propionate Hydrogen Oxidate Following the method of Example 7, 3,5-bistrifluoromethylbenzyl 2-amino-3-(3-indolyl)propionate hydrochloride (1.5 g) was treated with formaldehyde (0.7 ml of a 30% solution in water) and sodium cyanoborohydride (0.55 g) to give the title compound (420 mg) after purification by column chromatography on silica using ethyl acetate/petroleum ether (3:4) and treatment with oxalic acid in diethyl ether; mp 88°–90° C.; $^1$H NMR (360 MHz, DMSO) δ8.05 (1H, s), 7.91 (2H, s), 7.48 (1H, d, J=8 Hz), 7.30 (1H, d, J=8 Hz), 7.10 (1H, s), 7.02 (1H, t, J=8 Hz), 6.95 (1H, t, J=8 Hz), 5.26 (1H, d, J=12 Hz), 5.11 (1H, d, J=12 Hz), 3.55–3.50 (1H, m), 3.20–3.07 (2H, m), 2.43 (6H, s).

EXAMPLE 42

3,5-Dimethylbenzyl (2S)-2-t-butyloxycarbonylamino-3-(1-naphthyl)propionate

L-3-(1-Naphthyl)alanine (2 g), di-t-butyldicarbonate (3.0 g) and sodium carbonate (2.5 g) were stirred in a mixture of 1,4-dioxane (12 ml) and water (35 ml) at room temperature for 12 hours. To the solution was added water (100 ml), and the aqueous phase was washed with diethyl ether, acidified to pH3 with solid citric acid, and the product extracted into ethyl acetate. The organic phase was washed with water, dried (MgSO$_4$) and the solvent removed in vacuo to give a solid which was crystallised from ethyl acetate/petroleum ether.

This was dissolved in ethanol to which was added a solution of cesium carbonate (0.93 g) in water (10 ml). After the solution had been evaporated to dryness and re-evaporated repeatedly from a toluene solution, dimethylformamide (20 ml) and 3,5-dimethylbenzylbromide (1.3 g) were added. After stirring at room temperature for 16h, the mixture was diluted (water), and the product extracted into ethyl acetate. The organic phase was washed successively with water, 10% aqueous sodium carbonate, saturated brine and dried (MgSO$_4$). The solvent was removed in vacuo and the residue recrystallized from ethyl acetate/petrol to give the title compound, 0.5 g, mp 93°–94° C. $^1$H NMR (360 MHz, CDCl$_3$) δ8.09 (1H, d, J=8 Hz), 7.85 (1H, d, J=7 Hz), 7.75 (1H, d, J=8 Hz), 7.53–7.45 (2H, m), 7.34 (1H, t, J=7 Hz), 7.25 (1H, t, J=9 Hz), 6.93 (1H, s), 6.74 (2H, s), 5.07 (1H, bd, J=7 Hz), 5.00 (1H, d, J=12 Hz), 4.91 (1H, d, J=12 Hz), 4.78–4.76 (1H, m), 3.72–3.47 (2H, m)2.28 (6H, s), 1.40 (9H, s). m/z (CI$^+$) 434 (M+H). Found: C, 74.84; H, 7.30; N, 3.30. $C_{27}H_{31}NO_4$ requires C, 74.80; H, 7.21; N, 3.23%.

EXAMPLE 43

3,5-Dimethylbenzyl (2S)-2-amino-3-(1-naphthyl)propionate p-Toluenesulphonic Acid Salt The compound of Example 42 (0.4 g) was dissolved in trifluoroacetic acid for 40 minutes then evaporated to dryness. To a solution of the residue dissolved in ethanol (5 ml) was added 4-toluene sulfonic acid (0.16 g). The crystals which formed on standing were removed by filtration to give the title compound, 0.35 g, mp 164°–167° C. $^1$H NMR (360 MHz, CDCl$_3$) δ8.58 (3H, bs), 7.97 (1H, d, J=8.4 Hz), 7.77–7.73 (3H, m), 7.63 (1H, d, J=7.6 Hz), 7.38 (1H, t, J=7.2 Hz), 7.27 (1H, t, J=7.7 Hz), 7.19–7.11 (2H, m), 6.98 (2H, d, J=8.0 Hz), 6.78 (1H, s), 6.25 (1H, s), 4.62–4.52 (2H, m), 4.40 (1H, bd), 3.81 (1H, dd, J=5.4 Hz and 14.0 Hz), 3.52 (1H, dd, J=9.5 Hz and 14.0 Hz), 2.18 (3H, s), 2.12 (6H, s). Found: C, 68.67; H, 6.14; N, 2.80. $C_{22}H_{23}NO_2 \cdot C_7H_8O_3S$ requires C, 68.89; H, 6.18; N, 2.77%.

EXAMPLE 44

3,5-Dimethylbenzyl (2S)-2-acetamido-3-(1'-naphthyl)propionate

The compound of Example 2 (0.2 g) was dissolved in dry pyridine under nitrogen, and to this solution was added acetic anhydride (0.081 g). After stirring for 6 hours, water (10 ml) was added. The crystals which formed on standing were removed by filtration to give the title compound, 0.14 g, mp 136°–140° C. $^1$H NMR (360 MHz, CDCl$_3$) δ8.10 (1H, d, J=8.2 Hz), 7.85 (1H, d, J=7.6 Hz), 7.75 (1H, d, J=8.1 Hz), 7.53–7.45 (2H, m), 7.31 (1H, t, J=7.1 Hz), 7.15 (1H, d, J=6.5 Hz), 6.94 (1H, s), 6.73 (1H, s), 6.02 (1H, bd), 5.06 (1H, q, J=6.35 Hz), 4.94 (2H, ABq, J=12.0 Hz), 3.58 (2H, d, J=6.2 Hz), 2.23 (6H, s), 1.92 (3H, s). m/z (CI$^+$) 376 (M+H). Found: C, 76.38; H, 6.70; N, 3.81. $C_{24}H_{25}NO_3$ requires C, 76.78; H, 6.71; N, 3.73%.

EXAMPLE 45

3,5-Dimethylbenzyl 2-acetamido-3-phenylpropionate

The title compound was prepared in a manner analogous to that described in Examples 1 and 4, mp=97°–100° C. Found: C, 73.86; H, 7.34; N, 4.15: $C_{20}H_{18}NO_3$ requires: C, 73.82; H, 7.12; N, 4.30%.

EXAMPLE 46

2-Methoxybenzyl-3 (3-indolyl)-2-benzamidopropionate

Following the method of Example 12, 2-methoxybenzyl chloride gave the title compound which was recrystallized from ethyl acetate/petroleum ether, mp=144°–145° C.

EXAMPLE 47

N-(3,5-Bistrifluoromethylbenzyl)-2-acetamido-3 -(3-indolyl)propionamide

Following the method of Example 26b using acetic anhydride gave the title compound; mp=171°–173° C.; Found: C, 55.92; H, 4.06; N, 8.83. $C_{22}H_{19}F_6N_3O_2$ requires C, 56.05; H, 4.06; N, 8.91%.

EXAMPLE 48

3,5-Dimethylbenzyl (2S)-2-t-butyloxycarbonylamino-3-(2-naphthyl)propionate

The title compound was prepared from 3-(2-naphthyl)alanine in a manner analogous to that described in Example 42, mp 84°–86° C. $^1$H NMR (360 MHz, CDCl$_3$) δ7.79 (1H, d, J=5.3 Hz), 7.72–7.68 (2H, m), 7.51 (1H, s), 7.46–7.41 (2H, m), 7.18 (1H, d, J=7.4 Hz), 6.95 (1H, s), 6.85 (2H, s), 5.08–5.01 (3H, m), 4.71–4.69 (1H, m), 3.25 (2H, bs), 2.26 (6H, s), 1.40 (9H, s). m/z (CI$^+$) 434 (M+H).

EXAMPLE 49

3,5-Dimethylbenzyl (2S)-2-amino-3-(2-naphthyl)propionate p-Toluensulphonic Acid Salt The title compound was prepared in a manner analogous to that described in Example 43, mp 166°–169° C. $^1$H NMR (360 MHz, CDCl$_3$) δ8.39 (3H, bs, N$\underline{H}_3$), 7.66–7.64 (3H, m, Ar), 7.52–7.48 (3H, m, Ar), 7.38–7.25 (2H, m, Ar), 7.06 (2H, d, J=8.36 Hz, Ar), 6.96 (2H, d, J=7.9, Ar), 6.80 (1H, s, Ar), 6.47 (2H, s), 4.80 (1H, d, Jgem=12.0 Hz, OC$\underline{H}_A$H$_B$Ph), 4.68 (1H, d, Jgem=12.0 Hz, OC$\underline{H}_A$H$_B$Ph), 4.41 (1H, bs, C$\underline{H}$N), 3.40 (1H, dd, J=14.0 Hz, C$\underline{H}$HCN), 3.21 (1H, dd, J=14.0 Hz, 14.0 Hz, CH$\underline{H}$CN), 2.23 (3H, s), 2.07 (6H, s).

EXAMPLE 50

3,5-Dimethylbenzyl (2S)-2-acetamido-3-(2-naphthyl)propionate

The title compound was prepared in an analogous manner to that describer in Example 44, mp 96°–97° C. $^1$H NMR (360 MHz, CDCl$_3$) δ7.80–7.78 (1H, m, Ar), 7.71–7.67 (2H, m, Ar), 7.47–7.42 (3H, m, Ar), 7.13 (1H, d, J=10.0 Hz, 6.97 (1H, s, Ar), 6.88 (2H, s, Ar), 5.92 (1H, d, J=7.5 Hz), 5.06 (2H, d, J=3.1 Hz), 5.03–4.98 (1H, m), 3.29 (2H, d, J=5.8 Hz), 2.28 (6H, s), 1.98 (3H, s).

The following compounds were made using the method of Examples 1 and 6 using the appropriate benzyl halides:

EXAMPLE 51

3-Chlorobenzyl 3-(3-indolyl)-2-benzamidopropionate mp=146°–147° C.

EXAMPLE 52

2-Chlorobenzyl 3-(3-indolyl)-2 -benzamidopropionate mp=151°–152° C.

EXAMPLE 53

Benzyl 3-(3-indolyl)-2-benzamidopropionate mp=201°–202° C.

EXAMPLE 54

Benzyl 3-(3-indolyl)-2-acetamidopropionate mp=175°–176° C.

The following examples illustrate pharmaceutical compositions according to the invention.

EXAMPLE 55A Tablets containing 1–25 mg of compound

|  | Amount mg | | |
| --- | --- | --- | --- |
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

EXAMPLE 55B Tablets containing 26–100 mg of compound

|  | Amount mg | | |
| --- | --- | --- | --- |
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The compound of formula (I), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

EXAMPLE 56 Parenteral injection

|  | Amount mg |
| --- | --- |
| Compound of formula (I) | 1 to 100 mg |
| Citric Acid Monohydrate | 0.75 mg |
| Sodium Phosphate | 4.5 mg |
| Sodium Chloride | 9 mg |
| Water for injection | to 1 ml |

The sodium phosphate, citric acid monohydrate and sodium chloride are dissolved in a portion of the water. The compound of formula (I) is dissolved or suspended in the solution and made up to volume.

EXAMPLE 57 Topical formulation

|  | Amount mg |
| --- | --- |
| Compound of formula (I) | 1–10 g |
| Emulsifying Wax | 30 g |
| Liquid paraffin | 20 g |
| White Soft Paraffin | to 100 g |

The white soft paraffin is heated until molten. The liquid paraffin and emulsifying wax are incorporated and stirred until dissolved. The compound of formula (I) is added and stirring continued until dispersed. The mixture is then cooled until solid.

SUBSTANCE P ANTAGONISM ASSAY

A. Receptor Expression in Monkey Kidney Cell Line (COS)

To express the cloned human neurokinin-1-receptor (NK1R) transiently in COS, the cDNA for the human NK1R was cloned into the expression vector pCDM9 which was derived from pCDM8 (INVITROGEN) by inserting the ampicillin resistance gene (nucleotide 1973 to 2964 from BLUESCRIPT SK+ (trademark, STRATAGENE, La Jolla, Calif., USA)) into the Sac II site. Transfection of 20 ug of the plasmid DNA into 10 million COS cells was achieved by electroporation in 800 µl of transfection buffer (135 mM NaCl, 1.2 mM $CaCl_2$, 1.2 mM $MgCl_2$, 2.4 mM $K_2HPO_4$, 0.6 mM $KH_2PO_4$, 10 mM glucose, 10 mM N-2-hydroxyethyl-piperazine-N'-2-ethane sulphonic acid (HEPES) pH 7.4) at 260 V and 950 µF using the IBI GENEZAPPER (trademark IBI, New Haven, Conn., USA). The cells were incubated in 10% fetal calf serum, 2 mM glutamine, 100U/ml penicillin-streptomycin, and 90% DMEM media (GIBCO, Grand Island, N.Y., USA) in 5% $CO_2$ at 37° C. for three days before the binding assay.

B. Stable Expression in Chinese Hamster Ovarian Cell Line

To establish a stable cell line expressing cloned human NK1R, the cDNA was subcloned into the vector pRcCMV (INVITROGEN). Transfection of 20 ug of the plasmid DNA into CHO cells was achieved by electroporation in 800 µl of transfection buffer supplemented with 0.625 mg/ml Herring sperm DNA at 300 V and 950 µF using the IBI GENEZAPPER (IBI). The transfected cells were incubated in CHO media [10% fetal calf serum, 100 U/ml penicillin-streptomycin, 2 mM glutamine, 1/500 hypoxanthinethymidine (ATCC), 90% IMDM media (JRH BIOSCIENCES, Lenexa, Kans., USA), 0.7 mg/ml G418 (GIBCO)] in 5% $CO_2$ at 37° C. until colonies were visible. Each colony was separated and propagated. The cell clone with the highest number of human NK1R was selected for subsequent applications such as drug screening.

C. Assay Protocol using COS or CHO

The binding assay of human NK1R expressed in either COS or CHO cells is based on the use of $^{125}$I-substance P ($^{125}$I-SP, from DU PONT, Boston, Mass.) as a radioactively labeled ligand which competes with unlabeled substance P or any other ligand for binding to the human NK1R. Monolayer cell cultures of COS or CHO were dissociated by the non-enzymatic solution (SPECIALTY MEDIA, Lavellette, N.J.) and resuspended in appropriate volume of the binding buffer (50 mM Tris pH 7.5, 5 mM $MnCl_2$, 150 mM NaCl, 0.04 mg/ml bacitracin, 0.004 mg/ml leupeptin, 0.2 mg/ml BSA, 0.01 mM phosphoramidon) such that 200 µl of the cell suspension would give rise to about 10,000 cpm of specific $^{125}$I-SP binding (approximately 50,000 to 200,000 cells). In the binding assay, 200 ul of cells were added to a tube containing 20 ul of 1.5 to 2.5 nM of $^{125}$I-SP and 20 µl of unlabeled substance P or any other test compound. The tubes were incubated at 4° C. or at room temperature for 1 hour with gentle shaking. The bound 10 radioactivity was separated from unbound radioactivity by GF/C filter (BRANDEL, Gaithersburg, Md.) which was prewetted with 0.1% polyethylenimine. The filter was washed with 3 ml of wash buffer (50 mM Tris pH 7.5, 5 mM $MnCl_2$, 150 mM NaCl) three times and its radioactivity was determined by gamma counter.

The activation of phospholiphase C by NK1R may also be measured in CHO cells expressing the human NK1R by determining the accumulation of inositol monophosphate which is a degradation product of $IP_3$. CHO cells are seeded in 12-well plate at 250,000 cells per well. After incubating in CHO media for 4 days, cells are loaded with 5 µCi of $^3$H-myoinositol in 1 ml of media per well by overnight incubation. The extracellular radioactivity is removed by washing with phosphate buffered saline. LiCl is added to the well at final concentration of 10 mM with or without the test compound, and incubation is continued at 37° C. for 15 min. Substance P is added to the well at final concentration of 0.3 nM to activate the human NK1R. After 30 min of incubation at 37° C., the medium is removed and 0.1N HCl is added. Each well is sonicated at 4° C. and extracted with $CHCl_3$/methanol (1:1). The aqueous phase is applied to a 1 ml Dowex AG 1×8 ion exchange column. The column is washed with 0.1N formic acid followed by 0.025M ammonium formate-0.1N formic acid. The inositol monophosphate is eluted with 0.2M ammonium formate-0.1N formic acid and quantitated by beta counter.

The data in Table 1 were obtained for compounds of formula (I):

TABLE 1

SUBSTANCE P ANTAGONISM RESULTS

| Compound of Ex # | $IC_{50}$ @ NK1R (nM) |
| --- | --- |
| 1 | 110 |
| 2 | 140 |
| 3 | 800 |
| 4 | 50, 20 |
| 5 | 350 |
| 6 | 11, 24 |
| 7 | 560, 125 |
| 8 | 145, 50 |
| 9 | 7.5 |
| 10 | 5 |
| 11 | 190 |
| 12 | 170 |
| 13 | 62 |

TABLE 1-continued
SUBSTANCE P ANTAGONISM RESULTS

| Compound of Ex # | IC$_{50}$ @ NK1R (nM) |
| --- | --- |
| 14 | 390 |
| 15 | 2.5 |
| 16 | 90 |
| 17 | 280 |
| 18 | 280 |
| 19 | 190 |
| 20 | 90 |
| 21 | 180 |
| 22 | 260 |
| 23 | 260 |
| 24 | 70 |
| 25 | 1000 |
| 26 | 100 |
| 27 | >1000 |
| 28 | >1000 |
| 29 | 24% @ 1 μM |
| 30 | 200 |
| 31 | 140 |
| 32 | 190 |
| 33 | 32% @ 3 μM |
| 34 | 250 |
| 35 | 24% @ 1 μM |
| 36 | 480 |
| 37 | 280 |
| 38 | >1000 |
| 39 | 450 |
| 40 | 2 |
| 41 | 28 |
| 42 | 600 |
| 43 | 25% @ 1 μM |
| 44 | 130 |
| 45 | 400 |
| 46 | >1000 |
| 47 | 50% @ 1 μM |
| 48 | 38% @ 1 μM |
| 49 | 96% @ 10 μM |
| 50 | 55 |
| 51 | 32% @ 1 μM |
| 52 | 37% @ 1 μM |
| 53 | >1000 |
| 54 | >1000 |

We claim:
1. A compound of formula:

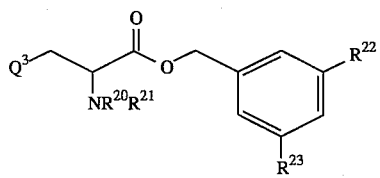

(ID)

wherein

Q$^3$ represents 3-indolyl, 3-benzothiophenyl, 3-indazolyl, 1-naphthyl, 2-naphthyl or phenyl optionally substituted by one or more substituents selected from C$_{1-6}$alkyl, C$_{2-6}$alkenyl, C$_{2-6}$alkynyl, halo, cyano, nitro, trifluoromethyl, trimethylsilyl, SR$^a$, SOR$^a$, SO$_2$R$^a$, OR$^a$, NR$^a$R$^b$, NR$^a$COR$^b$, NR$^a$COOR$^b$, COOR$^a$ or CONR$^a$R$^b$, where R$^a$ and R$^b$; independently represent H, C$_{1-6}$alkyl, phenyl or trifluoromethyl:

R$^{20}$ and R$^{21}$ each independently represents H; C$_{1-6}$alkyl, optionally substituted by hydroxy, cyano, COR$^c$, CO$_2$R$^c$, CONR$^c$R$^d$, or NR$^c$R$^d$ (where R$^c$ and R$^d$ each independently represent H, C$_{1-12}$alkyl or phenyl optionally substituted by one or more of C$_{1-6}$alkyl, C$_{1-6}$alkoxy, halo or trifluoromethyl); phenyl (C$_{1-4}$alkyl) (optionally substituted in the phenyl ring by one or more of C$_{1-6}$ alkyl, C$_{1-6}$alkoxy, halo and trifluoromethyl); COR$^c$, CO$_2$R$^c$, CONR$^c$R$^d$, CONR$^c$COOR$^d$; or SO$_2$R$^c$, where R$^c$ and R$^d$ are as above defined; and R$^{22}$ and R$^{23}$ each independently represent C$_{1-6}$alkyl, C$_{2-6}$alkenyl, C$_{2-6}$alkynyl, halo, cyano, nitro, trifluoromethyl, trimethylsilyl, OR$^a$, SR$^a$, SOR$^a$, NR$^a$R$^b$, NR$^a$COR$^b$, NR$^a$CO$_2$R$^b$, CO$_2$R$^a$ or CONR$^a$R$^b$, where R$^a$ and R$^b$ independently represent H, C$_{1-6}$alkyl, phenyl or trifluoromethyl) and pharmaceutically acceptable salts thereof.

2. A compound as claimed in claim 1 wherein one of R$^{20}$ and R$^{21}$ represents COR$^c$.

3. A compound as claimed in claim 1 selected from:

3,5-dimethylbenzyl 2-(1,1-dimethylethoxycarbonylamino)-3-(3-indolyl)propionate;

2-methoxybenzyl 2-(1,1-dimethylethoxycarbonylamino)-3-(3-indolyl)propionate;

3,5-dimethylbenzyl 2-acetamido-3-(3-indolyl)propionate;

3,5-dimethylbenzyl 2-cyclohexanecarboxamido-3-(3-indolyl)propionate;

3,5-dimethylbenzyl 3-(3-indolyl)-2-benzamidopropionate;

3,5-dimethylbenzyl 2-(N,N-dimethylamino)-3-(3-indolyl)propionate;

3,5-dimethylbenzyl 3-(indolyl)-2-(N,N,N-trimethylamino)propionate;

diphenylmethyl 2-acetamido-3-(3-indolyl)propionate;

3,5-(bis(trifluoromethyl)benzyl) 2-acetamido-3-(3-'benzo[b]thienyl)propionate;

3,5-(bis(trifluoromethyl)benzyl) 2-acetamido-3-(3-'indazolyl)propionate;

2-trifluoromethylbenzyl 3-(3-indolyl)-2-benzamidopropionate;

3-trifluoromethylbenzyl 3-(3-indolyl)-2-benzamidopropionate;

4-chlorobenzyl 3-(3-indolyl)-2-benzamidopropionate;

3,5-(bis(trifluoromethyl)benzyl) 2-acetamido-3-(3-indolyl)propionate;

3,5-dimethylbenzyl 2-(3-methylureido)-3-(3-indolyl)propionate;

3,5-dimethylbenzyl 2-ureido-3-(3-indolyl)propionate;

3,5-dimethylbenzyl 2-benzenesulphonamido-3-(3-indolyl)propionate;

3,5-dimethylbenzyl 2-methanesulphonamido-3-(3-indolyl)propionate;

3,5-dimethylbenzyl 2-methoxycarbonylamino-3-(3-indolyl)propionate;

3,5-dimethylbenzyl 2-ethylallophanato-3-(3-indolyl)propionate;

3,5-dimethylbenzyl-3-(3-indolyl)-2-(2,4-dichlorobenzamido)propionate;

3,5-dimethylbenzyl-3-(3-indolyl)-2-methyl-2-benzamidopropionate;

3,5-dimethylbenzyl 2-acetamido-3-(3,4-dichlorophenyl)propionate;

3,5-dimethylbenzyl 2(N,N-diethylamino)-3-(3-indolyl)propionate;

3,5-(bis(trifluoromethyl)benzyl) 3-(3-indilyl)-2-benzamidopropionate;

3,5-(bis(trifluoromethyl)benzyl) 2-(N,N-dimethylamino)-3-(3-indolyl)-propionate;

3,5-dimethylbenzyl (2S)-2-t-butyloxycarbonylamino-3-(1-naphthyl)propionate;

3,5-dimethylbenzyl (2S)-2-amino-3-(1-naphthyl)propionate;

3,5-dimethylbenzyl (2S)-2-acetamido-3-(1-naphthyl)propionate;

3,5-dimethylbenzyl 2-acetamido-3-phenylpropionate;

2-methoxybenzyl-3-(3-indolyl)-2-benzamidopropionate;

3,5-dimethylbenzyl (2S)-2-t-butyloxycarbonylamino-3-(2-naphthyl)propionate;

3,5-dimethylbenzyl (2S)-2-amino-3-(2-naphthyl)propionate;3,5-dimethylbenzyl (2S )-2-acetamido-3-(2-naphthyl)propionate;

3-chlorobenzyl-3-(3-indolyl)-2-benzamidopropionate;

2-chlorobenzyl-3-(3-indolyl)-2-benzamidopropionate;

benzyl-3-(3-indolyl)-2-benzamidopropionate;

benzyl-3-(3-indolyl)-2-acetamidopropionate;

and pharmaceutically acceptable salts and prodrugs thereof.

4. A pharmaceutical composition comprising a compound as claimed in claims 1 in association with a pharmaceutically acceptable carrier.

5. A method for the treatment of a physiological disorder associated with an excess of tachykinins, which method comprises admininstration to a patient in need thereof a tachykinin-reducing amount of a compound selected from compounds according to claim 1.

6. A method according to claim 5 wherein said physiological disorder is pain or inflammation.

7. A method according to claim 5 wherein said physiological disorder is migraine.

8. A method according to claim 5 wherein said physiological disorder is postherpetic neuralgia.

9. A compound as claimed in claim 3 being 3,5-(bis(trifluoromethyl)benzyl) 2-acetamido-3-indolyl)propionate.

* * * * *